US012686682B2

(12) United States Patent
Dolente et al.

(10) Patent No.: US 12,686,682 B2
(45) Date of Patent: Jul. 21, 2026

(54) INDAZOLE ACETYLENE DERIVATIVES

(71) Applicant: Hoffmann-La Roche Inc., Little Falls, NJ (US)

(72) Inventors: Cosimo Dolente, Allschwil (CH); Annick Goergler, Colmar (FR); David Stephen Hewings, Abingdon (GB); Georg Jaeschke, Basel (CH); Christa Ulrike Obst-Sander, Reinach BL (CH); Antonio Ricci, Biel-Benken (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 506 days.

(21) Appl. No.: 18/255,083

(22) PCT Filed: Nov. 29, 2021

(86) PCT No.: PCT/EP2021/083279

§ 371 (c)(1),
(2) Date: May 30, 2023

(87) PCT Pub. No.: WO2022/117477

PCT Pub. Date: Jun. 9, 2022

(65) Prior Publication Data

US 2024/0002390 A1 Jan. 4, 2024

(30) Foreign Application Priority Data

Dec. 1, 2020 (EP) .................................... 20210859

(51) Int. Cl.
*C07D 487/04* (2006.01)

(52) U.S. Cl.
CPC .................................. *C07D 487/04* (2013.01)

(58) Field of Classification Search
CPC .................................................... C07D 487/04
See application file for complete search history.

(56) References Cited

U.S. PATENT DOCUMENTS

| | | | |
|---|---|---|---|
| 10,882,848 | B2 | 1/2021 | Duplessis et al. |
| 11,117,890 | B2 | 9/2021 | Jaeschke et al. |
| 11,708,354 | B2 | 7/2023 | Duplessis et al. |
| 12,209,091 | B2 | 1/2025 | Duplessis et al. |
| 12,344,613 | B2 | 7/2025 | Dolente et al. |
| 12,479,849 | B2 | 11/2025 | Dolente et al. |
| 2021/0079005 | A1 | 3/2021 | Duplessis et al. |
| 2022/0112199 | A1 | 4/2022 | Dolente et al. |
| 2022/0135571 | A1 | 5/2022 | Dolente et al. |
| 2022/0315577 | A1 | 10/2022 | Jaeschke et al. |
| 2022/0315591 | A1 | 10/2022 | Dolente et al. |
| 2022/0315592 | A1 | 10/2022 | Dolente et al. |
| 2022/0315593 | A1 | 10/2022 | Dolente et al. |
| 2023/0034696 | A1 | 2/2023 | Jaeschke et al. |
| 2023/0054473 | A1 | 2/2023 | Dolente et al. |
| 2023/0057891 | A1 | 2/2023 | Hewings et al. |
| 2024/0018154 | A1 | 1/2024 | Dolente et al. |
| 2024/0059692 | A1 | 2/2024 | Dolente et al. |
| 2025/0313565 | A1 | 10/2025 | Jaeschke et al. |
| 2026/0007678 | A1 | 1/2026 | Jaeschke et al. |

FOREIGN PATENT DOCUMENTS

| | | | |
|---|---|---|---|
| WO | 2017/004383 | A1 | 1/2017 |
| WO | 2018/115218 | A1 | 6/2018 |
| WO | 2018/220149 | A1 | 12/2018 |
| WO | 2020/002487 | A1 | 1/2020 |
| WO | 2020/254544 | A1 | 12/2020 |
| WO | 2020/254546 | A1 | 12/2020 |
| WO | 2020/254547 | A1 | 12/2020 |
| WO | 2020/254562 | A1 | 12/2020 |
| WO | 2020/254565 | A1 | 12/2020 |
| WO | 2020/254568 | A1 | 12/2020 |
| WO | 2020/254572 | A1 | 12/2020 |
| WO | 2021/123084 | A1 | 6/2021 |
| WO | 2021/123087 | A1 | 6/2021 |

(Continued)

OTHER PUBLICATIONS

Gura et al., Systems for Identifying New Drugs are Often Faulty. Science, New Series, (1997), 278(5340), 1041-1042 (Year: 1997).*

(Continued)

*Primary Examiner* — Renee Claytor
*Assistant Examiner* — Christopher Lindsay Johnson

(57) ABSTRACT

The invention provides novel compounds having the general formula (I) or a pharmaceutically acceptable salt thereof, wherein $R^1$, $R^2$, $R^{2'}$, $R^3$, $R^4$ and $R^5$ are described herein. The compound of formula (I) can be used as a medicament.

(I)

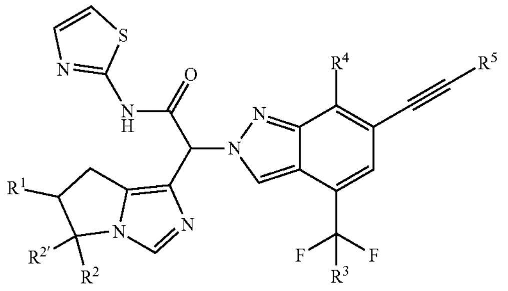

23 Claims, No Drawings

(56) References Cited

FOREIGN PATENT DOCUMENTS

| | | | |
|---|---|---|---|
| WO | 2022/117475 | A1 | 9/2022 |
| WO | 2022/117487 | A1 | 9/2022 |
| WO | 2023/217923 | A1 | 11/2023 |
| WO | 2023/217924 | A1 | 11/2023 |

OTHER PUBLICATIONS

Johnson et al., Relationships between drug activity in NCI preclinical in vitro and in vivo models and early clinical trials. British Journal of Cancer, (2001), 84(10), 1424-1431 (Year: 2001).*

Stewart et al., Known and putative mechanisms of resistance to EGFR targeted therapies in NSCLC patients with EGFR mutations—a review, Translational Lung Cancer Research, (2015), 4(1), 67-81 (Year: 2015).*

International Preliminary Report on Patentability—PCT/E P2021/083279 issued May 30, 2023, pp. 1-8.

International Search Report with Written Opinion—PCT/E P2021/083279 mailed Feb. 9, 2022, pp. 1-11.

* cited by examiner

INDAZOLE ACETYLENE DERIVATIVES

CROSS-REFERENCE TO RELATED APPLICATIONS

This application is a National Stage of International Application No. PCT/EP2021/083279, filed Nov. 29, 2021, which claims the benefit of European Patent Application No. 20210859.3, filed Dec. 1, 2020, the contents of which are incorporated by reference herein in their entirety.

The present invention relates to compounds that are selective allosteric inhibitors of T790M/L858R, T790M/L858R/C797S, L858R, and/or L858R/C797S containing EGFR mutants, their manufacture, pharmaceutical compositions containing it and their use as therapeutically active substances.

The invention relates in particular to a novel compound of formula (I)

(I)

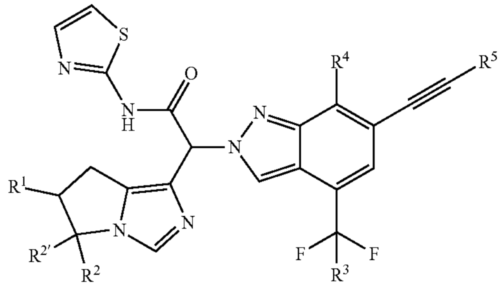

wherein $R^1$ is hydrogen or halogen;

$R^2$ and $R^{2'}$ are independently selected from hydrogen and alkyl;

or $R^2$ and $R^{2'}$, together with the carbon atom to which they are attached, form cycloalkyl;

$R^3$ is hydrogen or halogen;

$R^4$ is alkyl; and $R^5$ is hydroxyalkyl(heterocycloalkyl)alkyl;

or a pharmaceutically acceptable salt thereof.

The HER family receptor tyrosine kinases are mediators of cell growth, differentiation and survival. The receptor family includes four distinct members, i.e. epidermal growth factor receptor (EGFR, ErbB1, or HER1) HER2 (ErbB2), HER3 (ErbB3) and HER4 (ErbB4). Upon ligand binding the receptors form homo and heterodimers and subsequent activation of the intrinsic tyrosine kinase activity leads to receptor auto-phosphorylation and the activation of downstream signaling molecules (Yarden, Y., Sliwkowski, MX. Untangling the ErbB signalling network. Nature Review Mol Cell Biol. 2001 February; 2(2): 127-37). De-regulation of EGFR by overexpression or mutation has been implicated in many types of human cancer including colorectal, pancreatic, gliomas, head and neck and lung cancer, in particular non-small cell lung cancer (NSCLC) and several EGFR targeting agents have been developed over the years (Ciardiello, F., and Tortora, G. (2008). EGFR antagonists in cancer treatment. The New England journal of medicine 358, 1160-1174). Erlotinib (Tarceva®), a reversible inhibitor of the EGFR tyrosine kinase was approved in numerous countries for the treatment of recurrent NSCLC.

An impressive single agent activity of EGFR tyrosine kinase inhibitors is observed in a subset of NSCLC patients whose tumors harbor somatic kinase domain mutations, whereas clinical benefit in wild-type EGFR patients is greatly diminished (Paez, J. et al. (2004). EGFR mutations in lung cancer: correlation with clinical response to gefitinib therapy. Science (New York, NY 304, 1497-1500). The most common somatic mutations of EGFR are exon 19 deletions with delta 746-750 the most prevalent mutation and the exon 21 amino acid substitutions with L858R the most frequent mutation (Sharma S V, Bell D W, Settleman J, Haber D A. Epidermal growth factor receptor mutations in lung cancer. Nat Rev Cancer. 2007 March; 7(3): 169-81).

Treatment resistance arises frequently, often due to the secondary T790M mutation within the ATP site of the receptor. Some developed mutant-selective irreversible inhibitors are highly active against the T790M mutant, but their efficacy can be compromised by acquired mutation of C797S, that is the cysteine residue with which they form a key covalent bond (Thress, K. S. et al. Acquired EGFR C797S mutation mediates resistance to AZD9291 in non-small cell lung cancer harboring EGFR T790M. Nat. Med. 21, 560-562 (2015)). C797S mutation was further reported by Wang to be a major mechanism for resistance to T790M-targeting EGFR inhibitors (Wang et al. EGFR C797S mutation mediates resistance to third-generation inhibitors in T790M-positive non-small cell lung cancer, J Hematol Oncol. 2016; 9: 59). Additional mutations that cause resistance to Osimertinib are described by Yang, for example L718Q (Yang et al, Investigating Novel Resistance Mechanisms to Third-Generation EGFR Tyrosine Kinase Inhibitor Osimertinib in Non-Small Cell Lung Cancer Patients, Clinical Cancer Research, DOI: 10.1158/1078-0432.CCR-17-2310). Lu et al. (Targeting $EGFR^{L858R/T790M}$ and $EGFR^{L858R/T790M/C797S}$ resistance mutations in NSCLC: Current developments in medicinal chemistry, Med Res Rev 2018; 1-32) report in a review article on Targeting $EGFR^{L858R/T790M}$ and $EGFR^{L858R/T790MC797S}$ resistance mutations in NSCLC treatment.

As most available EGFR tyrosine kinase inhibitors target the ATP-site of the kinase, there is a need for new therapeutic agents that work differently, for example through targeting drug-resistant EGFR mutants.

Recent studies suggest that purposefully targeting allosteric sites might lead to mutant-selective inhibitors (Jia et al. Overcoming EGFR(T790M) and EGFR(C797S) resistance with mutant-selective allosteric inhibitors, June 2016, Nature 534, 129-132)

There is therefore an unmet need for the generation of selective molecules that specifically inhibit T790M/L858R, T790M/L858R/C797S, L858R and/or L858R/C797S containing EGFR mutants useful for the therapeutic and/or prophylactic treatment of cancer, in particular T790M and C797S containing EGFR mutants.

The compound of formula (I) as described herein does have improved EGFR potency and selectivity for T790M/L858R, T790M/L858R/C797S, L858R, and/or L858R/C797S containing EGFR mutants, in particular T790M and C797S containing EGFR mutants as well as improved physico-chemical properties.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, sec.-butyl, the isomeric pentyls, the isomeric hexyls, the isomeric heptyls and the isomeric octyls, particularly methyl, ethyl, propyl, butyl and pentyl. Particular examples of "alkyl" are methyl, ethyl, propyl, isopropyl, and tert.-butyl. Methyl is a particular example of "alkyl" in the compound of formula (I).

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular examples of "alkoxy" are methoxy, ethoxy and tert-butoxy.

The term "oxy", alone or in combination, signifies the —O— group.

The terms "halogen" or "halo", alone or in combination, signifies fluorine, chlorine, bromine or iodine and particularly fluorine or chlorine. A particular "halogen" or "halo" is fluorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Particular examples of "haloalkyl" are difluoromethyl and trifluoromethyl.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—$NH_2$), the secondary amino group (—NH—), or the tertiary amino group (—N—).

The term "alkylamino", alone or in combination, is alkyl group linked to a —NH— group. The term "dialkylamino" denotes two alkyl groups linked to a —N— atom.

The term "sulfonyl", alone or in combination, signifies the —$SO_2$— group.

The term "heterocycloalkyl", alone or in combination, denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having one or two ring atoms in common. Examples of "heterocycloalkyl" are morpholinyl, piperidinyl, azetidinyl and piperazinyl, A particular example of "heterocycloalkyl" is piperidinyl.

The term "cycloalkyl", alone or in combination, denotes a monovalent saturated cyclic hydrocarbon group of 3 to 8 ring carbon atoms. Examples of "cycloalkyl" are cyclopropyl, cyclobutanyl, cyclopentyl, cyclohexyl or cycloheptyl. A particular example of the "cycloalkyl" group is cyclopropyl.

The terms "piperidinyl" and "piperidyl" are interchangeable and signify, alone or in combination, a saturated monocycle comprising 5 carbon ring atoms and one nitrogen ring atom.

The term "pharmaceutically acceptable salt" refers to those salts of the compound of formula (I) which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of the compound of formula (I) are hydrochloride, formate and trifluoroacetate.

If one of the starting materials or a compound of formula (I) contains one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

The term "asymmetric carbon atom" means a carbon atom with four different substituents.

According to the Cahn-Ingold-Prelog Convention the asymmetric carbon atom can be of the "R" or "S" configuration.

The invention thus relates to:

A compound according to the invention wherein $R^1$ is hydrogen or fluoro;

A compound according to the invention wherein $R^1$ is hydrogen;

A compound according to the invention wherein $R^1$ is halogen;

A compound according to the invention wherein $R^1$ is fluoro;

A compound according to the invention wherein $R^2$ and $R^{2'}$ are independently selected from hydrogen or methyl; or $R^2$ and $R^{2'}$, together with the carbon atom to which they are attached, form cycloalkyl;

A compound according to the invention wherein $R^2$ and $R^{2'}$ are independently selected from hydrogen or alkyl; or $R^2$ and $R^{2'}$, together with the carbon atom to which they are attached, form cyclopropyl;

A compound according to the invention wherein $R^2$ and $R^{2'}$ are independently selected from hydrogen or methyl; or $R^2$ and $R^{2'}$, together with the carbon atom to which they are attached, form cyclopropyl;

A compound according to the invention wherein $R^2$ and $R^{2'}$ are both alkyl at the same time; or $R^2$ and $R^{2'}$, together with the carbon atom to which they are attached, form cycloalkyl;

A compound according to the invention wherein $R^2$ and $R^{2'}$ are both methyl at the same time; or $R^2$ and $R^{2'}$, together with the carbon atom to which they are attached, form cyclopropyl;

A compound according to the invention wherein $R^2$ and $R^{2'}$ are independently selected from hydrogen or methyl;

A compound according to the invention wherein $R^2$ and $R^{2'}$ are both alkyl at the same time;

A compound according to the invention wherein $R^2$ and $R^{2'}$ are both methyl at the same time;

A compound according to the invention wherein $R^2$ and $R^{2'}$, together with the carbon atom to which they are attached, form cycloalkyl;

A compound according to the invention wherein $R^2$ and $R^{2'}$, together with the carbon atom to which they are attached, form cyclopropyl;

A compound according to the invention wherein $R^3$ is hydrogen or fluoro;

A compound according to the invention wherein $R^3$ is hydrogen;

A compound according to the invention wherein $R^3$ is halogen;

A compound according to the invention wherein $R^3$ is fluoro;

A compound according to the invention wherein $R^4$ is methyl;

A compound according to the invention wherein $R^5$ is hydroxyalkyl(piperidinyl)alkyl;

A compound according to the invention wherein $R^5$ is hydroxymethyl(piperidinyl)methyl; and A compound according to the invention wherein $R^5$ is hydroxymethyl(heterocycloalkyl)methyl.

The invention further relates to a compound selected from

2-[4-(difluoromethyl)-6-[2-[4-[[4-(hydroxymethyl)-1-piperidyl]methyl]phenyl]ethynyl]-7-methyl-indazol-2-yl]-2-[(6R)-6-fluoro-6,7-dihydro-5H-pyrrolo[1,2-c]imidazol-1-yl]-N-thiazol-2-yl-acetamide;

2-[4-(difluoromethyl)-6-[2-[4-[[4-(hydroxymethyl)-1-piperidyl]methyl]phenyl]ethynyl]-7-methyl-indazol-2-yl]-2-(6,7-dihydro-5H-pyrrolo[1,2-c]imidazol-1-yl)-N-thiazol-2-yl-acetamide;

2-[(6R)-6-fluoro-6,7-dihydro-5H-pyrrolo[1,2-c]imidazol-1-yl]-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide;

2-(6,7-dihydro-5H-pyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide;

2-[4-(difluoromethyl)-6-[2-[4-[[4-(hydroxymethyl)-1-piperidyl]methyl]phenyl]ethynyl]-7-methyl-indazol-2-yl]-2-(5,5-dimethyl-6,7-dihydropyrrolo[1,2-c]imidazol-1-yl)-N-thiazol-2-yl-acetamide;

2-[4-(difluoromethyl)-6-[2-[4-[[4-(hydroxymethyl)-1-piperidyl]methyl]phenyl]ethynyl]-7-methyl-indazol-2-yl]-2-(5-ethyl-5-methyl-6,7-dihydropyrrolo[1,2-c]imidazol-1-yl)-N-thiazol-2-yl-acetamide;

2-(5-ethyl-5-methyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide; and 2-(5,5-dimethyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide;

or a pharmaceutically acceptable salt thereof.

The invention further relates to a compound selected from

2-[4-(difluoromethyl)-6-[2-[4-[[4-(hydroxymethyl)-1-piperidyl]methyl]phenyl]ethynyl]-7-methyl-indazol-2-yl]-2-(5,5-dimethyl-6,7-dihydropyrrolo[1,2-c]imidazol-1-yl)-N-thiazol-2-yl-acetamide;

2-[4-(difluoromethyl)-6-[2-[4-[[4-(hydroxymethyl)-1-piperidyl]methyl]phenyl]ethynyl]-7-methyl-indazol-2-yl]-2-(5-ethyl-5-methyl-6,7-dihydropyrrolo[1,2-c]imidazol-1-yl)-N-thiazol-2-yl-acetamide;

2-(5-ethyl-5-methyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide; and 2-(5,5-dimethyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide;

or a pharmaceutically acceptable salt thereof.

A certain embodiment of the invention relates to the compound of formula (I) or a pharmaceutically acceptable salt thereof, wherein the compound of formula (I) is 2-[4-(difluoromethyl)-6-[2-[4-[[4-(hydroxymethyl)-1-piperidyl]methyl]phenyl]ethynyl]-7-methyl-indazol-2-yl]-2-(5,5-dimethyl-6,7-dihydropyrrolo[1,2-c]imidazol-1-yl)-N-thiazol-2-yl-acetamide.

A certain embodiment of the invention relates to the compound of formula (I) or a pharmaceutically acceptable salt thereof, wherein the compound of formula (I) is 2-[4-(difluoromethyl)-6-[2-[4-[[4-(hydroxymethyl)-1-piperidyl]methyl]phenyl]ethynyl]-7-methyl-indazol-2-yl]-2-(5-ethyl-5-methyl-6,7-dihydropyrrolo[1,2-c]imidazol-1-yl)-N-thiazol-2-yl-acetamide.

A certain embodiment of the invention relates to the compound of formula (I) or a pharmaceutically acceptable salt thereof, wherein the compound of formula (I) is 2-(5-ethyl-5-methyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide.

A certain embodiment of the invention relates to the compound of formula (I) or a pharmaceutically acceptable salt thereof, wherein the compound of formula (I) is 2-(5,5-dimethyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide.

Processes for the manufacture of a compound of formula (I) as described herein are also an object of the invention.

The preparation of compounds of formula (I) of the present invention may be carried out in sequential or convergent synthetic routes. Syntheses of the compounds of the invention are shown in the following scheme 1 and in the description of specific examples. The skills required for carrying out the reactions and purifications of the resulting products are known to those skilled in the art. The substituents and indices used in the following description of the processes have the significance given herein before unless indicated to the contrary. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1
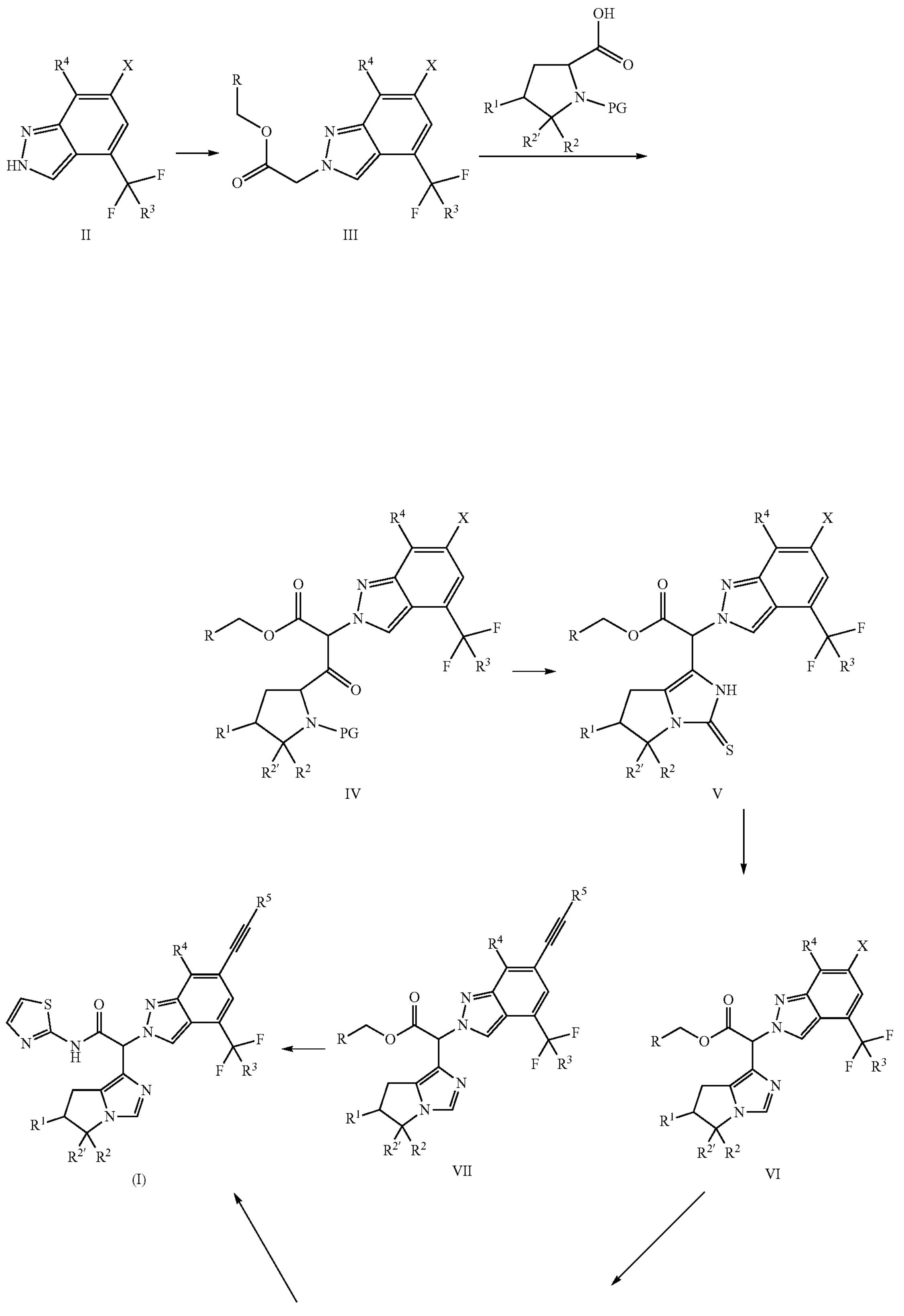

-continued

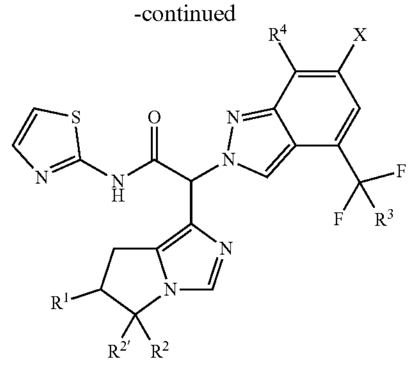

VIII

R = H or Me
PG = protecting group, e.g. BOC
X = Br, I, OMe, OiPr

In scheme 1, $R^1$, $R^2$, $R^3$, $R^4$ and $R^5$ are as defined herein.

An indazole of formula II can be alkylated with an alkylating agent such as ethyl bromoacetate or methyl bromoacetate in the presence or preferably in the absence of a base such as triethylamine or cesium carbonate in a solvent such as dimethylacetamide or acetonitrile at ambient or elevated temperature to give an indazole of formula III. This compound can be deprotonated with a base such as LDA or LHMDS and treated with a proline derivative that was pre-activated by treatment with e.g. CDI to give compounds of formula IV. This reaction can be performed in a solvent such as THF at a temperature from −78° to room temperature. The protecting group of compound IV can be cleaved by e.g. treatment with an acid such as HCl in dioxane or TFA. Subsequent treatment with potassium thiocyanate in a solvent such as EtOH at room temperature or slightly elevated temperature gives compounds of formula V. Conversion to imidazoles VI can be achieved by treatment with hydrogen peroxide in a solvent such as acetic acid or by treatment with Raney Nickel or by other methods known in the art. Introduction of acetylene-$R^5$ to give compounds VII can be performed using well-known methods such as Sonogashira reactions as well as other well-known synthetic methods for functional group transformations. Conversion to the compound of formula (I) can be achieved by saponification with a base such as LiOH or NaOH in solvents such as EtOH, THE and water and subsequent amide coupling with aminothiazole or a derivative thereof with a coupling agent such as HATU. Alternatively, a direct ester-amide conversion can be achieved using aminothiazole and reagents such as trimethylaluminum or isopropylmagnesium chloride.

A corresponding pharmaceutically acceptable salt of the compound of formula (I) with acids can be obtained by standard methods known to the person skilled in the art, e.g. by dissolving the compound of formula (I) in a suitable solvent such as e.g. dioxane or tetrahydrofuran and adding an appropriate amount of the corresponding acid. The products can usually be isolated by filtration or by chromatography. The conversion of a compound of formula (I) into a pharmaceutically acceptable salt thereof with a base can be carried out by treatment of such a compound with such a base. One possible method to form such a salt is e.g. by addition of 1/n equivalents of a basic salt such as e.g. M(OH)n, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts of the compound of formula (I) are hydrochloride, formate and trifluoroacetate.

Insofar as its preparation is not described in the examples, the compound of formula (I) as well as all intermediate products can be prepared according to analogous methods or according to the methods set forth herein.

It will be appreciated that the compound of general formula (I) in this invention may be derivatised at functional groups to provide derivatives which are capable of conversion to the parent compound in vivo.

The invention thus also relates to a process for the preparation of a compound of formula (I), comprising the reaction of a compound of formula (B1)

(B1)

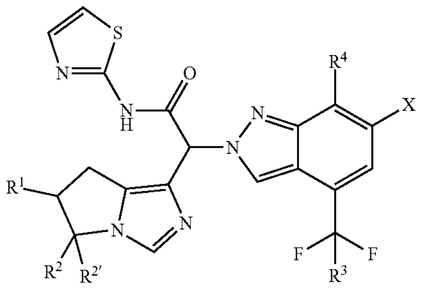

with a compound of formula (B2)

(B2)

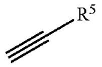

in presence of a base, a Pd(II) catalyst and a source of Cu(I), wherein $R^1$, $R^2$, $R^3$, $R^4$ and $R^5$ are as defined above and X is halogen.

In the above process, X is conveniently bromine.

In the process of the invention, the base can be for example piperidine, morpholine, diisopropylamine diethylamine, trimethylamine, cesium carbonate or a mixture thereof. Conveniently, the base is trimethylamine.

In the process of the invention, the catalyst can be for example bis-(triphenylphosphine)-palladium(II)dichloride.

The source of Cu(I) can be in particular copper(I)iodide.

The process of the invention can conveniently be carried out in a solvent, like for example DMF, THF, diethylamine, trimethylamine or a mixture thereof. Conveniently the solvent is DMF.

Convenient conditions for the process of the invention can be between around 20° C.-120° C., particularly between around 40° C.-110° C., more particularly between around 60° C.-100° C. Convenient conditions for the process can be around 80° C.

Convenient conditions for the process of the invention can be between around 0.25 h-20 h, particularly between around 0.5 h-10 h, more particularly between around 1 h-5 h. Convenient conditions for the process can be between around 1.5 h-2.5 h.

The invention also relates to a compound according to the invention when manufactured according to a process of the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compound of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compound of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention thus also relates in particular to:

A compound of formula (I) or a pharmaceutically acceptable salt thereof, for use as therapeutically active substance;

A pharmaceutical composition comprising a compound of formula (I) or a pharmaceutically acceptable salt thereof, and a therapeutically inert carrier;

A compound of formula (I) or a pharmaceutically acceptable salt thereof, for use in the treatment or prophylaxis of cancer;

A compound of formula (I) or a pharmaceutically acceptable salt thereof, for use in the treatment or prophylaxis of non-small cell lung cancer;

The use of a compound of formula (I) or a pharmaceutically acceptable salt thereof, for the treatment or prophylaxis of cancer, in particular non-small cell lung cancer;

The use of a compound of formula (I) or a pharmaceutically acceptable salt thereof, for the preparation of a medicament for the treatment or prophylaxis of cancer, in particular non-small cell lung cancer; and A method for the treatment or prophylaxis of cancer, in particular non-small cell lung cancer, which method comprises administering an effective amount of a compound of formula (I) or a pharmaceutically acceptable salt thereof, to a patient in need thereof.

A certain embodiment of the invention relates to a pharmaceutical composition comprising the compound of formula (I) as described herein, or a pharmaceutically acceptable salt thereof, and a pharmaceutically acceptable auxiliary substance.

A certain embodiment of the invention relates to the compound of formula (I) as described herein, or a pharmaceutically acceptable salt thereof, for the use in the treatment or prophylaxis of cancer, in particular non-small cell lung cancer, characterized by at least one EGFR mutation selected from T790M/L858R, T790M/L858R/C797S, L858R and L858R/C797S.

A certain embodiment of the invention relates to a method for the treatment or prophylaxis of cancer, in particular non-small cell lung cancer, wherein at least one EGFR mutation selected from T790M/L858R, T790M/L858R/C797S, L858R and L858R/C797S is present in the cancer, which method comprises administering an effective amount of a compound of formula (I) as described herein, or a pharmaceutically acceptable salt thereof, to a patient in need thereof.

Furthermore, the invention includes all substituents in its corresponding deuterated form, wherever applicable, of the compound of formula (I).

Furthermore, the invention includes all optical isomers, i.e. diastereoisomers, diastereomeric mixtures, racemic mixtures, all their corresponding enantiomers and/or tautomers as well as their solvates, wherever applicable, of the compound of formula (I).

The compound of formula (I) may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

Also an embodiment of the present invention is a compound of formula (I) as described herein, when manufactured according to any one of the described processes.

The compound of formula (I) or a pharmaceutically acceptable salt thereof can be used as medicament (e.g. in the form of pharmaceutical preparations). The pharmaceutical preparation can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compound of formula (I) or a pharmaceutically acceptable salt thereof can be processed with pharmaceutically inert, inorganic or organic adjuvants for the production of tablets, coated tablets, dragées, hard gelatin capsules, injection solutions or topical formulations. Lactose, corn starch or derivatives thereof, talc, stearic acid or the corresponding salts thereof can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg.

The formulation comprising a compound of formula (I) can be administered either by a single dose per day or per week, or by multiple doses (2 to 4) per day, or by multiple doses per week It will, however, be clear that the upper or lower limit given herein can be exceeded when this is shown to be indicated.

Pharmaceutical Compositions

The compound of formula (I) or a pharmaceutically acceptable salt thereof can be used as a therapeutically active substance, e.g. in the form of a pharmaceutical preparation. The pharmaceutical preparation can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compound of formula (I) or a pharmaceutically acceptable salt thereof can be processed with pharmaceutically inert, inorganic or organic carriers for the production of a pharmaceutical preparation. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparation can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. The pharmaceutical preparation can also contain still other therapeutically valuable substances.

Medicaments containing a compound of formula (I) or a pharmaceutically acceptable salt thereof and a therapeutically inert carrier are also provided by the present invention, as is a process for their production, which comprises bringing a compound of formula (I) and/or pharmaceutically acceptable salts thereof and, if desired, one or more other therapeutically valuable substances into a galenical administration form together with one or more therapeutically inert carriers.

The dosage can vary within wide limits and will, have to be adjusted to the individual requirements in each particular case. In the case of oral administration the dosage for adults can vary from about 0.01 mg to about 1000 mg per day of a compound of general formula (I) or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparation conveniently contains about 1-500 mg, particularly 1-100 mg, of a compound of formula (I). Examples of compositions according to the invention are:

EXAMPLE A

Tablets of the following composition are manufactured in the usual manner:

TABLE 1 possible tablet composition

| ingredient | mg/tablet 5 | 25 | 100 | 500 |
|---|---|---|---|---|
| (1) Compound of formula (I) | 5 | 25 | 100 | 500 |
| (2) Lactose Anhydrous DTG | 125 | 105 | 30 | 150 |
| (3) Sta-Rx 1500 | 6 | 6 | 6 | 60 |
| (4) Microcrystalline Cellulose | 30 | 30 | 30 | 450 |
| (5) Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 2 possible capsule ingredient composition

| ingredient | mg/capsule 5 | 25 | 100 | 500 |
|---|---|---|---|---|
| (1) Compound of formula (I) | 5 | 25 | 100 | 500 |
| (2) Hydrous Lactose | 159 | 123 | 148 | — |
| (3) Corn Starch | 25 | 35 | 40 | 70 |
| (4) Talk | 10 | 15 | 10 | 25 |
| (5) Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula (I), lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3 possible soft gelatin capsule ingredient composition

| ingredient | mg/capsule |
|---|---|
| Compound of formula (I) | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
|---|---|
| Gelatin | 75 |
| Glycerol 85 % | 32 |
| Karion 83 | 8 (dry matter) |
| Titan dioxide | 0.4 |
| Iron oxide yellow | 1.1 |
| Total | 116.5 |

Manufacturing Procedure

The compound of formula (I) is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5

| possible suppository composition | |
|---|---|
| ingredient | mg/supp. |
| Compound of formula (I) | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula (I) is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 6

| possible injection solution composition | |
|---|---|
| ingredient | mg/injection solution. |
| Compound of formula (I) | 3 |
| Polyethylene Glycol 400 | 150 |
| acetic acid | q.s. ad pH 5.0 |
| water for injection solutions | ad 1.0 ml |

Manufacturing Procedure

The compound of formula (I) is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7

| possible sachet composition | |
|---|---|
| ingredient | mg/sachet |
| Compound of formula (I) | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula (I) is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

Abbreviations

AcOH=acetic acid; ATP=adenosine triphosphate; CAS=chemical abstract service; CDI=1,1'-carbonyldiimidazole; DCM=dichloromethane; DME=dimethoxyethane; DMF=dimethylformamide; DMSO=diemethyl sulfoxide; EtOAc=ethyl acetate; EtOH=ethanol; HATU=hexafluorophosphate azabenzotriazole tetramethyl uronium; LDA=lithium diisopropylamide; MeOH=methanol; MS=mass spectrometry; NMR=nuclear magnetic resonance; rt=room temperature; THE=tetrahydrofuran.

The following examples are provided for illustration of the invention. They should not be considered as limiting the scope of the invention, but merely as being representative thereof.

EXAMPLE 1

2-[4-(Difluoromethyl)-6-[2-[4-[[4-(hydroxymethyl)-1-piperidyl]methyl]phenyl]ethynyl]-7-methyl-indazol-2-yl]-2-[(6R)-6-fluoro-6,7-dihydro-5H-pyrrolo[1,2-c]imidazol-1-yl]-N-thiazol-2-yl-acetamide

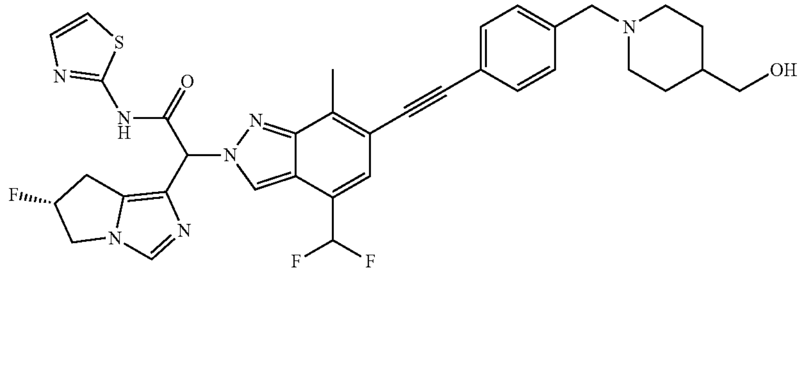 [SMILES: Cc1c(C#Cc2ccc(CN3CCC(CO)CC3)cc2)cc(C(F)F)c2cn(C(C(=O)Nc3nccs3)c3ncn4c3C[C@@H](F)C4)nc12]

Step 1: 1-Bromo-5-(difluoromethyl)-3-fluoro-2-methylbenzene

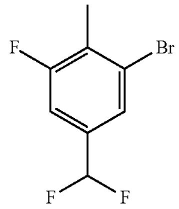

A solution of 3-bromo-5-fluoro-4-methylbenzaldehyde (CAS 1370411-47-4, 20.5 g, 89.7 mmol, Eq: 1.0) in DCM (98 mL) was cooled with ice bath. Morpholinosulfur trifluoride (CAS 51010-74-3, 24.8 g, 17.3 mL, 135 mmol, Eq: 1.5) was added in portions. The reaction mixture was stirred at 0-5° C. for 20 min, then stirred for 16 h at rt. With ice cooling, sat. aq. $NaHCO_3$ (300 mL) was added carefully. The reaction mixture was stirred for 1 h at rt. The reaction mixture was poured into DCM and washed with water. The organic layer was dried over $Na_2SO_4$ and concentrated in vacuo. The crude material was purified by flash chromatography (silica gel, 120 g, 100% pentane) to give the title compound as a colourless oil (18.6 g, 87% yield). $^1H$ NMR (300 MHz, chloroform-d) δ=7.50 (s, 1H), 7.16 (d, J=9.1 Hz, 1H), 6.57 (t, J=56.0 Hz, 1H), 2.50-2.22 (m, 3H)

Step 2: 6-Bromo-4-(difluoromethyl)-7-methyl-1H-indazole

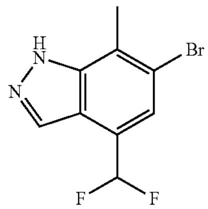

A solution of 1-bromo-5-(difluoromethyl)-3-fluoro-2-methylbenzene (Example 1, step 1) (26.4 g, 110 mmol, Eq: 1.0) in THE (240 mL) was cooled to −75° C. LDA (2 M in THF/heptane/ethylbenzene, 66.3 mL, 133 mmol, Eq: 1.2) was added dropwise below −70° C. The reaction mixture was stirred for 30 min at −75° C. Ethyl formate (16.4 g, 17.7 mL, 220 mmol, Eq: 2.0) was added below −70° C. The reaction mixture was stirred at −75° C. for 30 min. AcOH (16.6 g, 15.8 mL, 277 mmol, Eq: 2.5) was added below −55° C. The reaction mixture was allowed to warm up to rt and poured into EtOAc and washed with dilute aq. HCl, water and brine. The organic layer was dried over $Na_2SO_4$ and concentrated in vacuo to give presumed 4-bromo-6-(difluoromethyl)-2-fluoro-3-methylbenzaldehyde as a yellow oil (29.5 g) which was used without further purification.

The crude presumed 4-bromo-6-(difluoromethyl)-2-fluoro-3-methylbenzaldehyde (29.5 g) was dissolved in DME (150 mL). O-Methylhydroxylamine hydrochloride (10.2 g, 122 mmol, Eq: 1.84) and $K_2CO_3$ (30.6 g, 221 mmol, Eq: 3.34) were added. The reaction mixture was stirred for 2.5 h at 45° C. then filtered through sintered glass and washed with DME (2×). The filtrate was concentrated in vacuo. The oxime ether intermediate was dissolved in DMSO (150 mL). Hydrazine hydrate (83 g, 80.5 mL, 1.66 mol, Eq: 25) was added. The reaction mixture was stirred for 3 h at 110° C. The reaction mixture was poured into EtOAc/THF 5:1 and washed with water and brine. The organic layer was dried over $Na_2SO_4$ and concentrated in vacuo. The crude material was purified by flash chromatography (silica gel, 2×120 g, 0% to 30% EtOAc in heptane) to give the title compound as a white solid (13.5 g, 74% yield). m/z 258.9, 260.8 $[M+H]^+$, ESI pos, Br isotopes.

Step 3: Ethyl 2-[6-bromo-4-(difluoromethyl)-7-methyl-indazol-2-yl]acetate

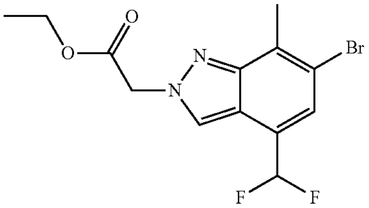 [SMILES: CCOC(=O)Cn1cc2c(C(F)F)cc(Br)c(C)c2n1]

To a solution of 6-bromo-4-(difluoromethyl)-7-methyl-1H-indazole (Example 1, step 2) (19 g, 72.8 mmol, Eq: 1.0) in DMF (75 mL) was added ethyl 2-bromoacetate (18.2 g, 12.2 mL, 109 mmol, Eq: 1.5). The reaction mixture was stirred for 16 h at 100° C. The reaction mixture was poured into EtOAc and washed with water and brine. The organic layer was dried over $Na_2SO_4$ and concentrated in vacuo. The crude material was purified by flash chromatography (silica gel, 2×120 g, 0% to 20% EtOAc in heptane) to give the title compound as a yellow solid (21.2 g, 80% yield). m/z 346.9, 348.8, $[M+H]^+$, ESI pos, Br isotopes.

Step 4: tert-Butyl (2S,4R)-2-[2-[6-bromo-4-(difluoromethyl)-7-methyl-indazol-2-yl]-3-ethoxy-3-oxo-propanoyl]-4-fluoro-pyrrolidine-1-carboxylate

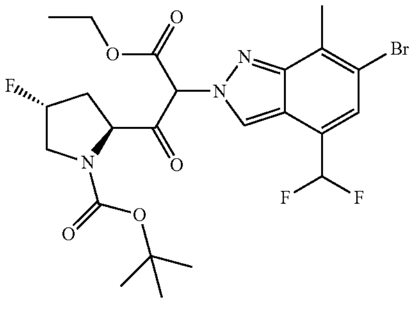 [SMILES: CCOC(=O)C(C(=O)[C@@H]1C[C@@H](F)CN1C(=O)OC(C)(C)C)n1cc2c(C(F)F)cc(Br)c(C)c2n1]

Preparation of tert-butyl (2S,4R)-4-fluoro-2-(imidazole-1-carbonyl)pyrrolidine-1-carboxylate:

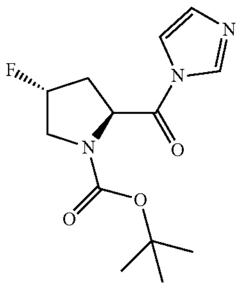 [SMILES: CC(C)(C)OC(=O)N1C[C@H](F)C[C@H]1C(=O)n1ccnc1]

To a solution of (2S,4R)-1-tert-butoxycarbonyl-4-fluoro-pyrrolidine-2-carboxylic acid (CAS 203866-14-2, 30 g, 129 mmol, Eq: 1.0) in DCM (300 mL) was added 1,1'-carbonyldiimidazole (25 g, 154 mmol, Eq: 1.2) in portions at 0° C. The reaction mixture was stirred for 3 h at rt. The reaction mixture was washed with water (3×) and 1M aq. $NaHCO_3$ (1×). The organic layer was dried over $Na_2SO_4$ and concentrated in vacuo at 30° C. to give tert-butyl (2S,4R)-4-fluoro-2-(imidazole-1-carbonyl)pyrrolidine-1-carboxylate (36.6 g, 129 mmol, 100% yield) as a white solid which was stored at −20° C. prior to use. $^1$H NMR (chloroform-d, 300 MHz) δ 8.27 (s, 1H), 7.56 (br d, 1H, J=1.4 Hz), 7.15 (br d, 1H, J=12.1 Hz), 4.9-5.2 (m, 1H), 3.6-4.1 (m, 2H), 2.0-2.9 (m, 2H), 1.2-1.5 (m, 9H).

KO$^t$Bu (4.53 g, 40.3 mmol, Eq: 2.0) was dissolved in THF (18 mL). The reaction mixture was cooled to −55° C. A solution of ethyl 2-[6-bromo-4-(difluoromethyl)-7-methyl-indazol-2-yl]acetate (Example 1, step 3) (7 g, 20.2 mmol, Eq: 1.0) in THE (24 mL) was added dropwise below −50° C. The reaction mixture was stirred for 1 h between −50° C. and −55° C. A solution of previously-prepared tert-butyl (2S,4R)-4-fluoro-2-(imidazole-1-carbonyl)pyrrolidine-1-carboxylate (6.85 g, 24.2 mmol, Eq: 1.2) in THE (50 mL) was added dropwise below −50° C. The reaction mixture was stirred for 15 min at −50° C., then allowed to warm up to −30° C. 10% aqueous citric acid (60 mL) was added below −20° C., and the mixture was stirred for 1 h at 0° C. The reaction mixture was poured into EtOAc and washed with water and brine. The organic layer was dried over $Na_2SO_4$ and concentrated in vacuo at 30° C. to give the title compound as a yellow amorphous semisolid (12.9 g, 20.2 mmol, 88% purity, 100% yield). m/z 562.1, 563.9 $[M+H]^+$, ESI pos, Br isotopes.

Step 5: Ethyl 2-[6-bromo-4-(difluoromethyl)-7-methyl-indazol-2-yl]-2-[(6R)-6-fluoro-3-thioxo-2,5,6,7-tetrahydropyrrolo[1,2-c]imidazol-1-yl]acetate

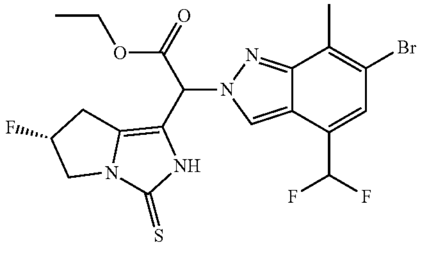 [SMILES: CCOC(=O)C(c1[nH]c(=S)n2c1C[C@@H](F)C2)n1cc2c(C(F)F)cc(Br)c(C)c2n1]

To a solution of tert-butyl (2S,4R)-2-[2-[6-bromo-4-(difluoromethyl)-7-methyl-indazol-2-yl]-3-ethoxy-3-oxo-propanoyl]-4-fluoro-pyrrolidine-1-carboxylate (Example 1, step 4) (12.9 g, 20.2 mmol, Eq: 1.0) in ethanol (24 mL) was added HCl (1.25 M in ethanol, 80.6 mL, 101 mmol, Eq: 5.0). The reaction mixture was stirred for 1 h at 55° C. The reaction mixture was cooled to rt, then water (6 mL) and potassium thiocyanate (2.55 g, 26.2 mmol, Eq: 1.3) were added. The reaction mixture was stirred for 30 min at rt. The ethanol was removed in vacuo at 30° C., and pyridine (23.9 g, 24.5 mL, 302 mmol, Eq: 15) was added. The reaction mixture was stirred at rt for 75 min. The reaction mixture was poured into EtOAc and washed with 2 N aq. HCl (until the aqueous phase was pH 1), water and brine. The organic layer was dried over $Na_2SO_4$ and concentrated in vacuo to give the title compound as a yellow semisolid (9.65 g, 60% purity, 57% yield). m/z 502.9, 505.9 $[M+H]^+$, ESI pos, Br isotopes.

Step 6: Ethyl 2-[6-bromo-4-(difluoromethyl)-7-methyl-indazol-2-yl]-2-[(6R)-6-fluoro-6,7-dihydro-5H-pyrrolo[1,2-c]imidazol-1-yl]acetate

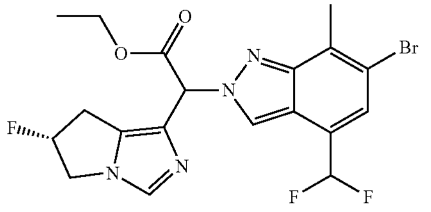 [SMILES: CCOC(=O)C(c1ncn2c1C[C@@H](F)C2)n1cc2c(C(F)F)cc(Br)c(C)c2n1]

To a suspension of p-toluenesulfonic acid monohydrate (10.9 g, 57.5 mmol, Eq: 5.0) in acetonitrile (70 mL) was added hydrogen peroxide (35% aq., 8.38 g, 7.42 mL, 86.3 mmol, Eq: 7.5) dropwise at 0-3° C. to give a colorless solution. After 10 min, ethyl 2-[6-bromo-4-(difluoromethyl)-7-methyl-indazol-2-yl]-2-[(6R)-6-fluoro-3-thioxo-2,5,6,7-tetrahydropyrrolo[1,2-c]imidazol-1-yl]acetate (Example 1, step 5) (9.65 g, 11.5 mmol, Eq: 1.0) in acetonitrile (28 mL) was added dropwise below 8° C. The reaction mixture was stirred for 1.5 h at 0° C. The reaction mixture was poured into EtOAc and washed with $Na_2CO_3$ solution and brine. The organic layer was dried over $Na_2SO_4$ and concentrated in vacuo. The crude material was purified by flash chromatography (silica gel, 120 g, 0% to 60% (EtOAc/EtOH/aq. $NH_3$ 75:25:2) in heptane) to give the title compound as a yellow foam (3.96 g, 73% yield). m/z 469.1, 471.1 $[M+H]^+$, ESI pos.

Step 7: 2-[6-Bromo-4-(difluoromethyl)-7-methyl-indazol-2-yl]-2-[(6R)-6-fluoro-6,7-dihydro-5H-pyrrolo[1,2-c]imidazol-1-yl]-N-thiazol-2-yl-acetamide

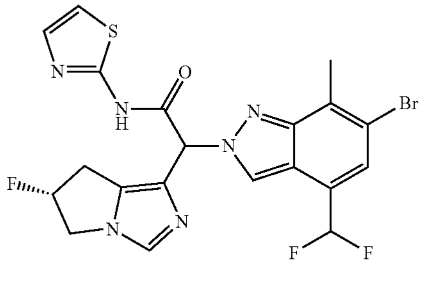 [SMILES: Cc1c(Br)cc(C(F)F)c2cn(C(C(=O)Nc3nccs3)c3ncn4c3C[C@@H](F)C4)nc12]

Ethyl 2-[6-bromo-4-(difluoromethyl)-7-methyl-indazol-2-yl]-2-[(6R)-6-fluoro-6,7-dihydro-5H-pyrrolo[1,2-c]imidazol-1-yl]acetate (Example 1, step 6) (200 mg, 0.424 mmol) was dissolved in 2 ml of methanol and 2 ml of THF. LiOH (1M in water) (0.4 ml, 0.424 mmol, Eq: 1.0) was added at room temperature. The mixture was stirred for 2 hours at room temperature. The reaction mixture was concentrated in vacuo to dryness and the residue was dissolved in 2 ml of DMF. Thiazol-2-amine (42 mg, 0.424 mmol, Eq: 1.0), Hunig's base (0.37 ml, 2.12 mmol, Eq: 5.0) and HATU (194 mg, 0.509 mmol, Eq: 1.2) were added at room temperature. The mixture was stirred at room temperature for 90 minutes. The reaction mixture was extracted with water and two times with ethyl acetate. The organic layers were extracted with water, dried over sodium sulfate and concentrated to dryness. The crude product was purified by flash chromatography on a silica gel column eluting with a dichloromethane:methanol 100:0 to 90:10 gradient to obtain the desired product (115 mg, 49% yield) as a light yellow solid, MS: m/e=527.1 (M+H$^+$).

Step 8: [1-[(4-Ethynylphenyl)methyl]-4-piperidyl]methanol

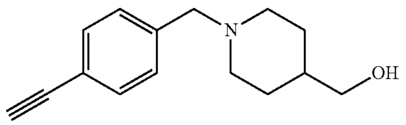 [SMILES: C#Cc1ccc(CN2CCC(CO)CC2)cc1]

4-Ethynylbenzaldehyde (20.5 g, 157.5 mmol) was dissolved in 525 ml of dichloromethane. Piperidin-4-ylmethanol (20 g, 173.2 mmol, Eq: 1.1) and sodium triacetoxyborohydride (53.4 g, 252.0 mmol, Eq: 1.6) were added at room temperature. The mixture was stirred at room temperature for 4 hours. The reaction mixture was extracted with 1M sodium carbonate solution and two times with dichloromethane. The organic layers were dried over sodium sulfate and concentrated to dryness to obtain the desired product (34.8 g, 91% yield) as a light yellow solid, MS: m/e=527.1 (M+H$^+$).

Step 9: [1-[(4-Ethynylphenyl)methyl]-4-piperidyl]methanol hydrochloride

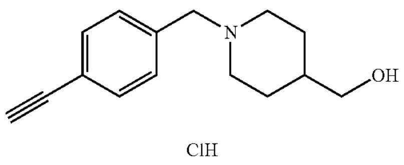 [SMILES: C#Cc1ccc(CN2CCC(CO)CC2)cc1 ; Cl]

[1-[(4-Ethynylphenyl)methyl]-4-piperidyl]methanol (Example 1, step 8) (34.8 g) was dissolved in 200 ml of tetrahydrofuran. 4 M Hydrogen chloride solution in 1,4-dioxane (39.4 ml, 158 mmol, Eq: 1.0) was added drop wise at 10-20° C. A white precipitate was formed and stirred for 2 hours. The precipitate was collected by filtration, washed with three 50 ml portions of tetrahydrofuran and dried in vacuo to give the title compound (38.6 g, 92%) as a white solid, MS: m/e=527.1 (M+H$^+$).

Step 10: 2-[4-(Difluoromethyl)-6-[2-[4-[[4-(hydroxymethyl)-1-piperidyl]methyl]phenyl]ethynyl]-7-methyl-indazol-2-yl]-2-[(6R)-6-fluoro-6,7-dihydro-5H-pyrrolo[1,2-c]imidazol-1-yl]-N-thiazol-2-yl-acetamide

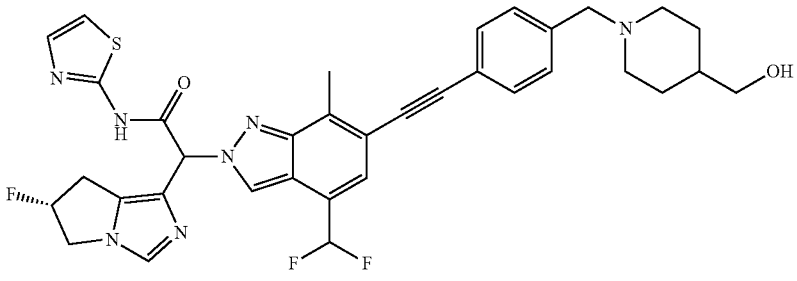 [SMILES: Cc1c(C#Cc2ccc(CN3CCC(CO)CC3)cc2)cc(C(F)F)c2cn(C(C(=O)Nc3nccs3)c3ncn4c3C[C@@H](F)C4)nc12]

2-[6-Bromo-4-(difluoromethyl)-7-methyl-indazol-2-yl]-2-[(6R)-6-fluoro-6,7-dihydro-5H-pyrrolo[1,2-c]imidazol-1-yl]-N-thiazol-2-yl-acetamide (Example 1, step 7) (100 mg, 0.19 mmol) and [1-[(4-ethynylphenyl)methyl]-4-piperidyl] methanol hydrochloride (Example 1, step 9) (76 mg, 0.286 mmol, Eq: 1.5) were dissolved in 5 ml of DMF. Triethylamine (0.1 ml, 0.76 mmol, Eq: 4.0), bis-(triphenylphosphine)-palladium(II)dichloride (7 mg, 0.01 mmol, Eq: 0.05), triphenylphosphine (5 mg, 0.019 mmol, Eq: 0.1) and copper (I)iodide (2 mg, 0.01 mmol, Eq: 0.05) were added and the mixture was stirred for 2 hours at 80° C. The reaction mixture was extracted with water and three times with dichloromethane. The organic layers were dried over sodium sulfate and concentrated to dryness. The crude product was purified by flash chromatography on a silica gel column eluting with a dichloromethane:methanol 100:0 to 75:25 gradient to obtain the desired product (7 mg, 5% yield) as a light yellow oil, MS: m/e=674.5 (M+H$^+$).

EXAMPLE 2

2-[4-(Difluoromethyl)-6-[2-[4-[[4-(hydroxymethyl)-1-piperidyl]methyl]phenyl]ethynyl]-7-methyl-indazol-2-yl]-2-(6,7-dihydro-5H-pyrrolo[1,2-c]imidazol-1-yl)-N-thiazol-2-yl-acetamide

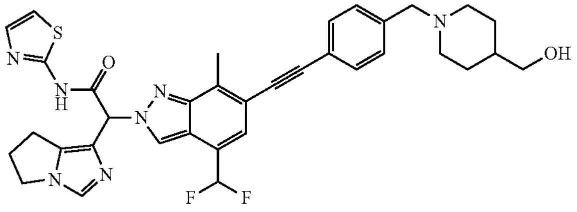 [SMILES: Cc1c(C#Cc2ccc(CN3CCC(CO)CC3)cc2)cc(C(F)F)c2cn(C(C(=O)Nc3nccs3)c3ncn4c3CCC4)nc12]

Step 1: tert-Butyl (2R)-2-[2-[6-bromo-4-(difluoromethyl)-7-methylindazol-2-yl]-3-ethoxy-3-oxopropanoyl] pyrrolidine-1-carboxylate

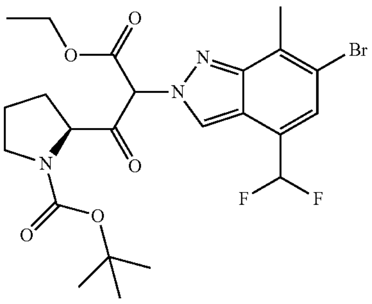 [SMILES: CCOC(=O)C(C(=O)[C@@H]1CCCN1C(=O)OC(C)(C)C)n1cc2c(C(F)F)cc(Br)c(C)c2n1]

Ethyl 2-[6-bromo-4-(difluoromethyl)-7-methyl-indazol-2-yl]acetate, prepared as described in Intermediate 1, Step 3 (0.65 g, 1.87 mmol, Eq: 1.0) was dissolved in THE (7.58 mL) and cooled to −75° C. LDA (2 M in THF, 1.12 mL, 2.25 mmol, Eq: 1.20) was added dropwise within 5 min. The reaction mixture was stirred for 40 min at −75° C. A solution of tert-butyl (2S)-2-(imidazole-1-carbonyl)pyrrolidine-1-carboxylate (prepared from (2S)-1-tert-butoxycarbonyl-4-fluoro-pyrrolidine-2-carboxylic acid by analogy with Intermediate 1, Step 4) (0.77 g, 2.9 mmol, Eq: 1.55) in THE (7.58 mL) was added slowly at −75° C., stirred for 30 min at −75° C. then allowed to warm up to rt and stirred for 18 h at rt. After the addition of sat. aq. $NH_4Cl$, the reaction mixture was extracted twice with EtOAc. The organic layers were washed with water. The combined organic layers were dried over $Na_2SO_4$ and concentrated in vacuo to give the title compound (1.41 g, 72% purity, 99%, yield) which was used in the next step without further purification. m/z 544.1, 546.0 [M+H]$^+$, ESI pos. Br isotopes.

Step 2: Ethyl 2-[6-bromo-4-(difluoromethyl)-7-methyl-indazol-2-yl]-2-(3-thioxo-2,5,6,7-tetrahydro-pyrrolo[1,2-c]imidazol-1-yl)acetate

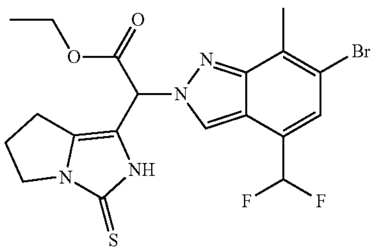 [SMILES: CCOC(=O)C(c1[nH]c(=S)n2c1CCC2)n1cc2c(C(F)F)cc(Br)c(C)c2n1]

By analogy with Example 1, Step 5, tert-butyl (2R)-2-[2-[6-bromo-4-(difluoromethyl)-7-methylindazol-2-yl]-3-ethoxy-3-oxopropanoyl]pyrrolidine-1-carboxylate (1.4 g, 72% purity, 1.85 mmol) was treated with HCl 4 M in dioxane and potassium thiocyanate to give the title compound as a brown oil (1.07 g, 85% purity, 100% yield) which was used in the next step without further purification. m/z 485.0, 486.9 [M+H]$^+$, ESI pos, Br isotopes.

Step 3: Ethyl 2-[6-bromo-4-(difluoromethyl)-7-methyl-indazol-2-yl]-2-(6,7-dihydro-5H-pyrrolo[1,2-c]imidazol-1-yl)acetate

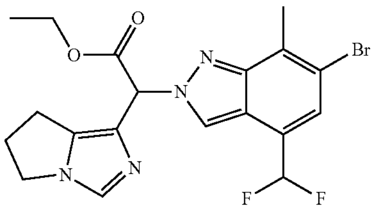 [SMILES: CCOC(=O)C(c1ncn2c1CCC2)n1cc2c(C(F)F)cc(Br)c(C)c2n1]

By analogy with Example 1, Step 6, ethyl 2-[6-bromo-4-(difluoromethyl)-7-methyl-indazol-2-yl]-2-(3-thioxo-2,5,6,7-tetrahydropyrrolo[1,2-c]imidazol-1-yl)acetate (1.06 g, 85% purity, 1.86 mmol) was treated with hydrogen peroxide and p-toluenesulfonic acid monohydrate to give the title compound as a yellow foam (360 mg, 43% yield). m/z 453.0, 454.9 $[M+H]^+$, ESI pos, Br isotopes.

Step 4: 2-[6-Bromo-4-(difluoromethyl)-7-methyl-indazol-2-yl]-2-(6,7-dihydro-5H-pyrrolo[1,2-c]imidazol-1-yl)-N-thiazol-2-yl-acetamide

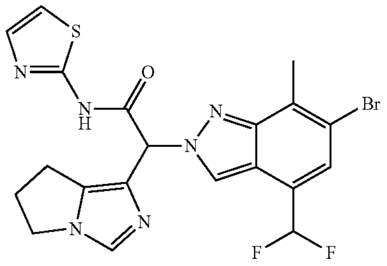 [SMILES: Cc1c(Br)cc(C(F)F)c2cn(C(C(=O)Nc3nccs3)c3ncn4c3CCC4)nc12]

The title compound was obtained as a light yellow foam, MS: m/e=509.1/511.1 $(M+H^+)$, using chemistry similar to that described in Example 1, step 7 starting from ethyl 2-[6-bromo-4-(difluoromethyl)-7-methyl-indazol-2-yl]-2-(6,7-dihydro-5H-pyrrolo[1,2-c]imidazol-1-yl)acetate (Example 2, step 3) and thiazol-2-amine.

Step 5: 2-[4-(Difluoromethyl)-6-[2-[4-[[4-(hydroxymethyl)-1-piperidyl]methyl]phenyl]ethynyl]-7-methyl-indazol-2-yl]-2-(6,7-dihydro-5H-pyrrolo[1,2-c]imidazol-1-yl)-N-thiazol-2-yl-acetamide

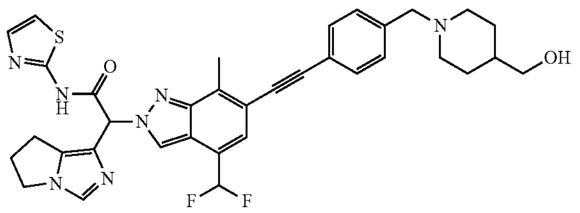 [SMILES: Cc1c(C#Cc2ccc(CN3CCC(CO)CC3)cc2)cc(C(F)F)c2cn(C(C(=O)Nc3nccs3)c3ncn4c3CCC4)nc12]

The title compound was obtained as a brown solid, MS: m/e=656.5 $(M+H^+)$, using chemistry similar to that described in Example 1, step 10 starting from 2-[6-bromo-4-(difluoromethyl)-7-methyl-indazol-2-yl]-2-(6,7-dihydro-5H-pyrrolo[1,2-c]imidazol-1-yl)-N-thiazol-2-yl-acetamide (Example 2, step 4) and [1-[(4-ethynylphenyl)methyl]-4-piperidyl]methanol hydrochloride (Example 1, step 9).

EXAMPLE 3

2-[(6R)-6-Fluoro-6,7-dihydro-5H-pyrrolo[1,2-c]imidazol-1-yl]-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide

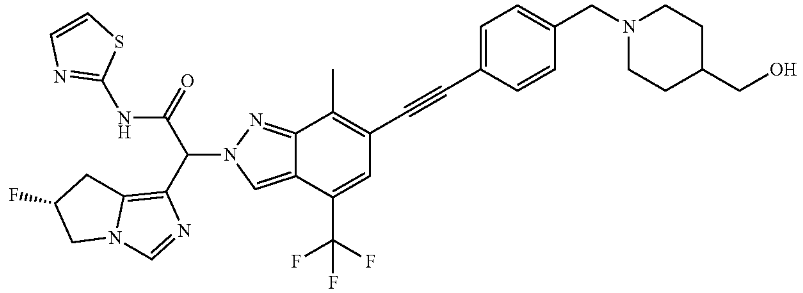 [SMILES: Cc1c(C#Cc2ccc(CN3CCC(CO)CC3)cc2)cc(C(F)(F)F)c2cn(C(C(=O)Nc3nccs3)c3ncn4c3C[C@@H](F)C4)nc12]

Step 1: 1-Bromo-3-fluoro-2-methyl-5-(trifluoromethyl)benzene

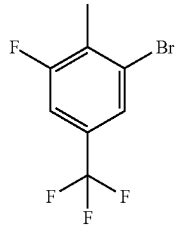

1-Bromo-3-fluoro-5-(trifluoromethyl)benzene (12.7 g) was dissolved in Tetrahydrofuran (60 ml) and cooled to −75° C. LDA, 2.1 mol/1 in THE (27.4 ml) was added dropwise. After stirring for 30 min at −75° C., iodomethane (8.16 g) was added dropwise. The mixture was allowed to warm to room temperature overnight. After addition of half saturated ammonium chloride solution and ethyl acetate the layers were separated, once more extracted with ethyl acetate. The org layers were washed with water, combined, dried over sodium sulphate and concentrated. The residual brown liquid (15.42 g) was bulb-to-bulb distilled at ~10 mbar and 60-80° C. oven temperature to give the title compound as colorless liquid (11.91 g) containing 8 mol % of ethylbenzene.

Step 2: 4-Bromo-2-fluoro-3-methyl-6-(trifluoromethyl)benzaldehyde

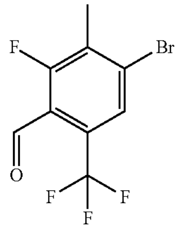

In analogy to the synthesis of 4-bromo-3,6-dichloro-2-fluorobenzaldehyde, 1-bromo-3-fluoro-2-methyl-5-(trifluoromethyl)benzene was first treated with LDA in Tetrahydrofuran at −75° C. followed by treatment with N,N-dimethylformamide. Workup in analogy to the synthesis of 4-bromo-3,6-dichloro-2-fluorobenzaldehyde gave the crude title compound as brown liquid.

Step 3: 6-Bromo-7-methyl-4-(trifluoromethyl)-1H-indazole

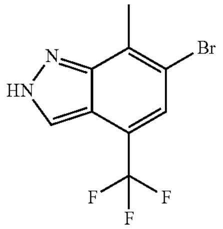

In analogy to the synthesis of 6-bromo-4-chloro-7-methoxy-2H-indazole, a solution of 4-bromo-2-fluoro-3-methyl-6-(trifluoromethyl)benzaldehyde was heated with an excess of hydrazine hydrate to give the title compound as light yellow solid. MS: m/e=278.9 ($[M+H]^+$, Br)

Step 4: Ethyl 2-(6-bromo-7-methyl-4-(trifluoromethyl)-2H-indazol-2-yl)acetate

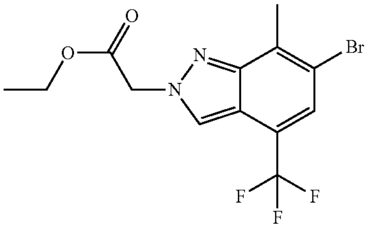 [SMILES: CCOC(=O)Cn1cc2c(C(F)(F)F)cc(Br)c(C)c2n1]

The title compound was obtained as a light yellow solid, MS: m/e=365.1/367.1 ($M+H^+$), using chemistry similar to that described in Example 1, step 3 starting from 6-bromo-7-methyl-4-(trifluoromethyl)-1H-indazole (Example 3, step 3).

Step 5: tert-Butyl (2S,4R)-2-(2-(6-bromo-7-methyl-4-(trifluoromethyl)-2H-indazol-2-yl)-3-ethoxy-3-oxopropanoyl)-4-fluoropyrrolidine-1-carboxylate

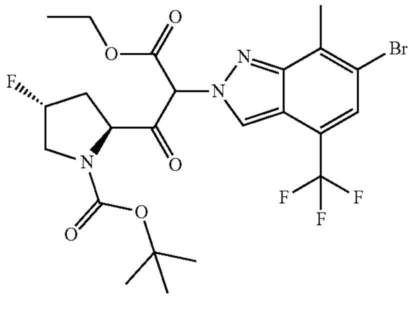 [SMILES: CCOC(=O)C(C(=O)[C@@H]1C[C@@H](F)CN1C(=O)OC(C)(C)C)n1cc2c(C(F)(F)F)cc(Br)c(C)c2n1]

In analogy to Example 1, step 4, (2S,4R)-1-(tert-butoxycarbonyl)-4-fluoropyrrolidine-2-carboxylic acid was treated with carbonyldiimidazole to give solution A. Ethyl 2-(6-bromo-7-methyl-4-(trifluoromethyl)-2H-indazol-2-yl)acetate was deprotonated with LDA and treated with solution A at −78° C. After stirring at room temperature overnight and workup in analogy to Example 1, step 4, the crude title compound was obtained which was used for the next step without further purification. MS: m/e=578.4 ($[M-H]^-$)

Step 6: Ethyl 2-(6-bromo-7-methyl-4-(trifluoromethyl)-2H-indazol-2-yl)-2-((R)-6-fluoro-3-thioxo-2,5,6,7-tetrahydro-3H-pyrrolo[1,2-c]imidazol-1-yl) acetate

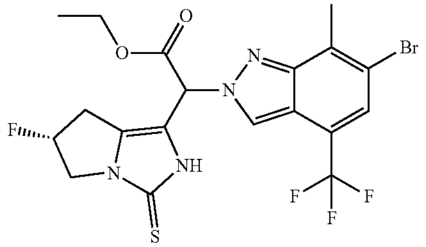 [SMILES: CCOC(=O)C(c1[nH]c(=S)n2c1C[C@@H](F)C2)n1cc2c(C(F)(F)F)cc(Br)c(C)c2n1]

In analogy to Example 1, step 5, tert-butyl (2S,4R)-2-(2-(6-bromo-7-methyl-4-(trifluoromethyl)-2H-indazol-2-yl)-3-ethoxy-3-oxopropanoyl)-4-fluoropyrrolidine-1-carboxylate was deprotected using HCl in dioxane followed by reaction with potassium thiocyanate to give the crude title compound which was used for the next step without further purification. MS: m/e=519.3 ($[M-H]^-$)

Step 6: Ethyl 2-(6-bromo-7-methyl-4-(trifluoromethyl)-2H-indazol-2-yl)-2-((R)-6-fluoro-6,7-dihydro-5H-pyrrolo[1,2-c]imidazol-1-yl)acetate

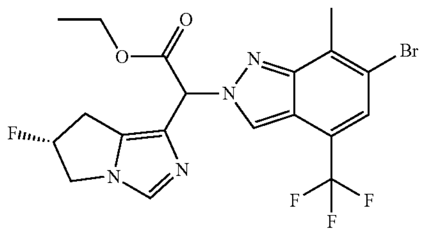 [SMILES: CCOC(=O)C(c1ncn2c1C[C@@H](F)C2)n1cc2c(C(F)(F)F)cc(Br)c(C)c2n1]

In analogy to Example 1, step 6, ethyl 2-(6-bromo-7-methyl-4-(trifluoromethyl)-2H-indazol-2-yl)-2-((R)-6-fluoro-3-thioxo-2,5,6,7-tetrahydro-3H-pyrrolo[1,2-c]imidazol-1-yl)acetate was treated with hydrogen peroxide in AcOH to give the title compound as brown solid. MS: m/e=489.3 ($[M+H]^+$)

Step 7: 2-[6-Bromo-7-methyl-4-(trifluoromethyl)indazol-2-yl]-2-[(6R)-6-fluoro-6,7-dihydro-5H-pyrrolo[1,2-c]imidazol-1-yl]-N-thiazol-2-yl-acetamide

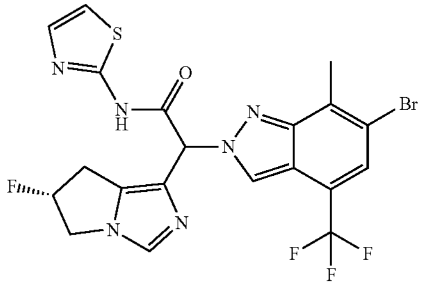 [SMILES: Cc1c(Br)cc(C(F)(F)F)c2cn(C(C(=O)Nc3nccs3)c3ncn4c3C[C@@H](F)C4)nc12]

The title compound was obtained as a white solid, MS: m/e=543.1/545.1 ($M+H^+$), using chemistry similar to that described in Example 1, step 7 starting from ethyl 2-(6-bromo-7-methyl-4-(trifluoromethyl)-2H-indazol-2-yl)-2-((R)-6-fluoro-6,7-dihydro-5H-pyrrolo[1,2-c]imidazol-1-yl) acetate (Example 3, step 6) and thiazol-2-amine.

Step 8: 2-[(6R)-6-Fluoro-6,7-dihydro-5H-pyrrolo[1,2-c]imidazol-1-yl]-2-[6-[2-(4-formylphenyl)ethynyl]-7-methyl-4-(trifluoromethyl)indazol-2-yl]-N-thiazol-2-yl-acetamide

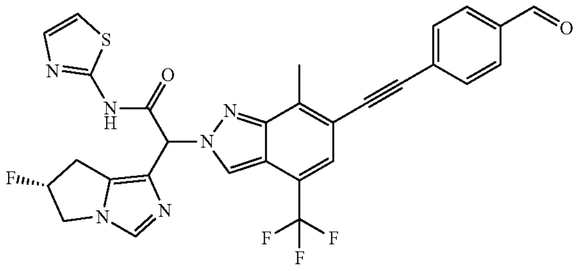 [SMILES: Cc1c(C#Cc2ccc(C=O)cc2)cc(C(F)(F)F)c2cn(C(C(=O)Nc3nccs3)c3ncn4c3C[C@@H](F)C4)nc12]

The title compound was obtained as a white solid, MS: m/e=593.4 ($M+H^+$), using chemistry similar to that described in Example 1, step 10 starting from 2-[6-bromo-7-methyl-4-(trifluoromethyl)indazol-2-yl]-2-[(6R)-6-fluoro-6,7-dihydro-5H-pyrrolo[1,2-c]imidazol-1-yl]-N-thiazol-2-yl-acetamide (Example 3, step 7) and 4-ethynylbenzaldehyde.

Step 9: 2-[(6R)-6-Fluoro-6,7-dihydro-5H-pyrrolo[1,2-c]imidazol-1-yl]-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide

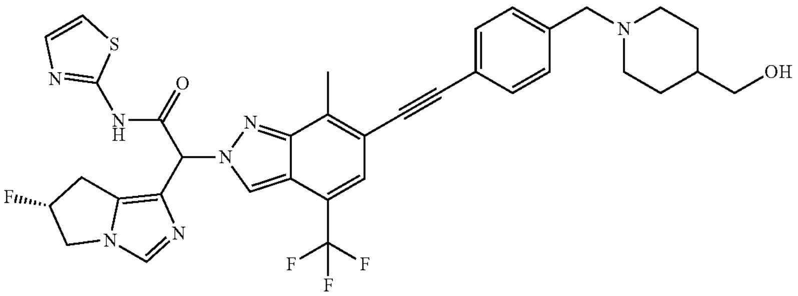 [SMILES: Cc1c(C#Cc2ccc(CN3CCC(CO)CC3)cc2)cc(C(F)(F)F)c2cn(C(C(=O)Nc3nccs3)c3ncn4c3C[C@@H](F)C4)nc12]

The title compound was obtained as a white solid, MS: m/e=690.6 ($M+H^+$), using chemistry similar to that described in Example 1, step 8 starting from 2-[(6R)-6-fluoro-6,7-dihydro-5H-pyrrolo[1,2-c]imidazol-1-yl]-2-[6-[2-(4-formylphenyl)ethynyl]-7-methyl-4-(trifluoromethyl) indazol-2-yl]-N-thiazol-2-yl-acetamide (Example 3, step 8) and piperidin-4-ylmethanol.

EXAMPLE 4

2-(6,7-Dihydro-5H-pyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide

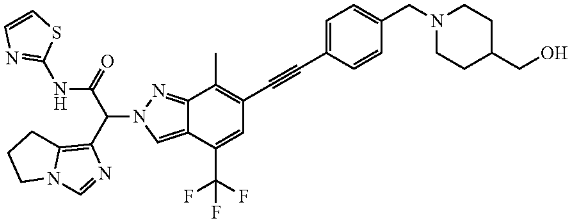 [SMILES: Cc1c(C#Cc2ccc(CN3CCC(CO)CC3)cc2)cc(C(F)(F)F)c2cn(C(C(=O)Nc3nccs3)c3ncn4c3CCC4)nc12]

Step 1: tert-Butyl (2R)-2-(2-(6-bromo-7-methyl-4-(trifluoromethyl)-2H-indazol-2-yl)-3-ethoxy-3-oxopropanoyl)pyrrolidine-1-carboxylate

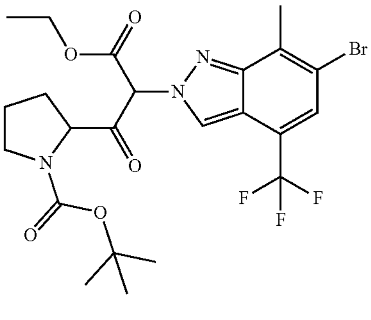 [SMILES: CCOC(=O)C(C(=O)C1CCCN1C(=O)OC(C)(C)C)n1cc2c(C(F)(F)F)cc(Br)c(C)c2n1]

(tert-Butoxycarbonyl)-L-proline (2.38 g) was dissolved under argon in THE (15 ml) and cooled to 0° C. CDI (1.79 g) was added. The temp was allowed to rise to rt and the mixture was stirred overnight at rt. The mixture was diluted with ethyl acetate and washed with water, sodium bicarbonate solution and brine. The organic layers were combined, dried over sodium sulfate, concentrated and dried. Ethyl 2-(6-bromo-7-methyl-4-(trifluoromethyl)-2H-indazol-2-yl) acetate (Example 3, step 4) (2.6 g) was dissolved in THE (15 ml) and cooled to −76° C. LDA (2 M, 4.45 ml) was added dropwise at −76° C. The reaction mixture was stirred at −76° C. for 40 min. Then, a solution of the above prepared activated amide in THE (15 ml) was added dropwise at −75° C. The mixture was stirred 30 min at −75° C., let slowly warm up to rt and stirred 5 h at rt. The reaction mixture was quenched with saturated $NH_4Cl$-solution and then extracted with EtOAc. The aqueous layer was back extracted with EtOAc. The organic layers were washed with brine. The organic layers were combined, dried over sodium sulfate, filtered and concentrated in vacuo to give the crude title compound (6 g, approx. 68% purity) which was used for the next step without further purification. MS: m/e=564.1 ($[M+H]^+$)

Step 2: Ethyl 2-(6-bromo-7-methyl-4-(trifluoromethyl)-2H-indazol-2-yl)-2-(6,7-dihydro-5H-pyrrolo[1,2-c]imidazol-1-yl)acetate

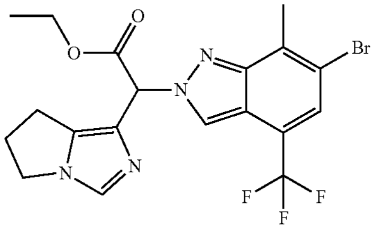 [SMILES: CCOC(=O)C(c1ncn2c1CCC2)n1cc2c(C(F)(F)F)cc(Br)c(C)c2n1]

In analogy to Example 1, steps 5 and 6, tert-butyl (2R)-2-(2-(6-bromo-7-methyl-4-(trifluoromethyl)-2H-indazol-2-yl)-3-ethoxy-3-oxopropanoyl)pyrrolidine-1-carboxylate was deprotected using HCl in dioxane followed by reaction with potassium thiocyanate followed by reaction with hydrogen peroxide in AcOH to give the title compound as light yellow solid. MS: m/e=471.2 ([M+H]+)

Step 3: 2-[6-Bromo-7-methyl-4-(trifluoromethyl) indazol-2-yl]-2-(6,7-dihydro-5H-pyrrolo[1,2-c]imidazol-1-yl)-N-thiazol-2-yl-acetamide

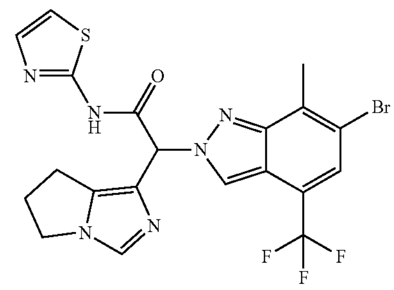 [SMILES: Cc1c(Br)cc(C(F)(F)F)c2cn(C(C(=O)Nc3nccs3)c3ncn4c3CCC4)nc12]

The title compound was obtained as a light yellow foam, MS: m/e=525.1/527.1 (M+H$^+$), using chemistry similar to that described in Example 1, step 7 starting from ethyl 2-(6-bromo-7-methyl-4-(trifluoromethyl)-2H-indazol-2-yl)-2-(6,7-dihydro-5H-pyrrolo[1,2-c]imidazol-1-yl)acetate (Example 4, step 2) and thiazol-2-amine.

Step 4: 2-(6,7-Dihydro-5H-pyrrolo[1,2-c]imidazol-1-yl)-2-[6-[2-[4-[[4-(hydroxymethyl)-1-piperidyl] methyl]phenyl]ethynyl]-7-methyl-4-(trifluoromethyl)indazol-2-yl]-N-thiazol-2-yl-acetamide

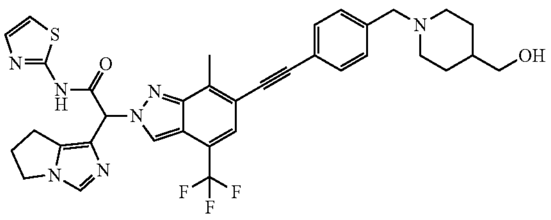 [SMILES: Cc1c(C#Cc2ccc(CN3CCC(CO)CC3)cc2)cc(C(F)(F)F)c2cn(C(C(=O)Nc3nccs3)c3ncn4c3CCC4)nc12]

The title compound was obtained as a light yellow solid, MS: m/e=674.4 (M+H$^+$), using chemistry similar to that described in Example 1, step 10 starting from 2-[6-bromo-7-methyl-4-(trifluoromethyl)indazol-2-yl]-2-(6,7-dihydro-5H-pyrrolo[1,2-c]imidazol-1-yl)-N-thiazol-2-yl-acetamide (Example 4, step 3) and [1-[(4-ethynylphenyl)methyl]-4-piperidyl]methanol hydrochloride (Example 1, step 9).

EXAMPLE 5

2-[4-(Difluoromethyl)-6-[2-[4-[[4-(hydroxymethyl)-1-piperidyl]methyl]phenyl]ethynyl]-7-methyl-indazol-2-yl]-2-(5,5-dimethyl-6,7-dihydropyrrolo[1,2-c] imidazol-1-yl)-N-thiazol-2-yl-acetamide

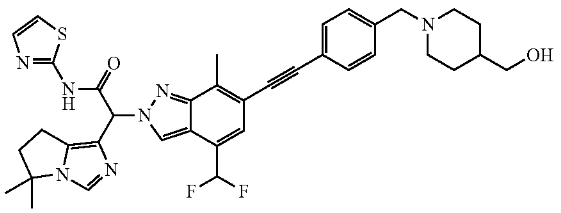 [SMILES: Cc1c(C#Cc2ccc(CN3CCC(CO)CC3)cc2)cc(C(F)F)c2cn(C(C(=O)Nc3nccs3)c3ncn4c3CCC4(C)C)nc12]

Step 1: (5S)-5-[2-[6-Bromo-4-(difluoromethyl)-7-methyl-indazol-2-yl]-3-ethoxy-3-keto-propanoyl]-2,2-dimethyl-pyrrolidine-1-carboxylic acid tert-butyl ester

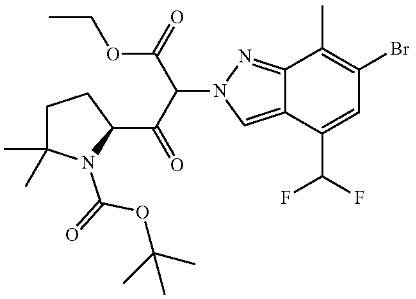 [SMILES: CCOC(=O)C(C(=O)[C@@H]1CCC(C)(C)N1C(=O)OC(C)(C)C)n1cc2c(C(F)F)cc(Br)c(C)c2n1]

In analogy to Example 1, step 4, (2S)-1-tert-butoxycarbonyl-5,5-dimethyl-proline was treated with carbonyldiimidazole to give solution A. 2-[6-Bromo-4-(difluoromethyl)-7-methyl-indazol-2-yl]acetic acid ethyl ester was deprotonated with LDA and treated with solution A at −78° C. After stirring at room temperature overnight and workup in analogy to Example 1, step 4, the crude title compound was obtained as a white foam and used for the next step without further purification. MS: m/e=572.3 ([M+H]$^+$)

Step 2: 2-[6-Bromo-4-(difluoromethyl)-7-methyl-indazol-2-yl]-2-(5,5-dimethyl-6,7-dihydropyrrol[1,2-c]imidazol-1-yl)acetic acid ethyl ester

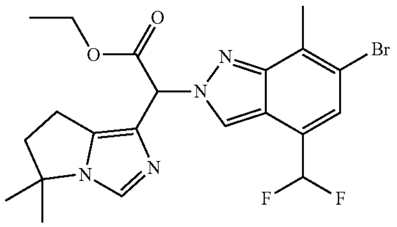 [SMILES: CCOC(=O)C(c1ncn2c1CCC2(C)C)n1cc2c(C(F)F)cc(Br)c(C)c2n1]

In analogy to Example 1, step 5, (5S)-5-[2-[6-bromo-4-(difluoromethyl)-7-methyl-indazol-2-yl]-3-ethoxy-3-ketopropanoyl]-2,2-dimethyl-pyrrolidine-1-carboxylic acid tert-butyl ester was deprotected using HCl in dioxane followed by reaction with potassium thiocyanate to give the crude intermediate which was used for the next step without further purification.

In analogy to Example 1, step 6, the intermediate was treated with hydrogen peroxide in AcOH to give the title compound as a colorless oil. MS: m/e=489.3 ([M+H]$^+$)

Step 3: 2-[6-Bromo-4-(difluoromethyl)-7-methyl-indazol-2-yl]-2-(5,5-dimethyl-6,7-dihydropyrrol[1,2-c]imidazol-1-yl)-N-thiazol-2-yl-acetamide

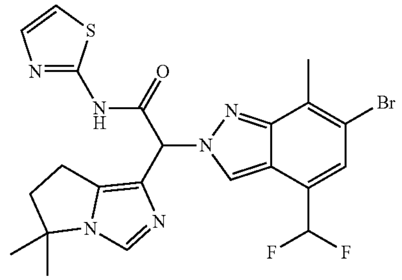 [SMILES: Cc1c(Br)cc(C(F)F)c2cn(C(C(=O)Nc3nccs3)c3ncn4c3CCC4(C)C)nc12]

The title compound was obtained as a light yellow foam, MS: m/e=537.2 (M+H$^+$), using chemistry similar to that described in Example 1, step 7 starting from 2-[6-bromo-4-(difluoromethyl)-7-methyl-indazol-2-yl]-2-(5,5-dimethyl-6,7-dihydropyrrol[1,2-c]imidazol-1-yl)acetic acid ethyl ester (Example 5, step 2) and thiazol-2-amine.

Step 4: 2-[4-(Difluoromethyl)-6-[2-(4-formylphenyl)ethynyl]-7-methyl-indazol-2-yl]-2-(5,5-dimethyl-6,7-dihydropyrrolo[1,2-c]imidazol-1-yl)-N-thiazol-2-yl-acetamide

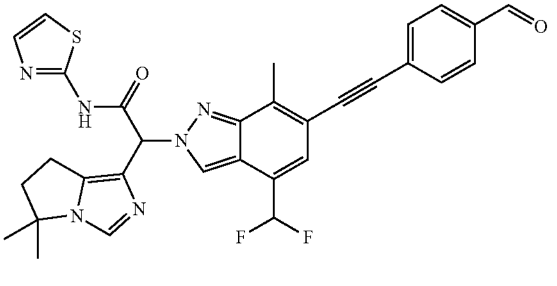 [SMILES: Cc1c(C#Cc2ccc(C=O)cc2)cc(C(F)F)c2cn(C(C(=O)Nc3nccs3)c3ncn4c3CCC4(C)C)nc12]

The title compound was obtained as a dark brown foam, MS: m/e=585.4 (M+H$^+$), using chemistry similar to that described in Example 1, step 10 starting from 2-[6-bromo-4-(difluoromethyl)-7-methyl-indazol-2-yl]-2-(5,5-dimethyl-6,7-dihydropyrrol[1,2-c]imidazol-1-yl)-N-thiazol-2-yl-acetamide (Example 5, step 3) and 4-ethynylbenzaldehyde.

Step 5: 2-[4-(Difluoromethyl)-6-[2-[4-[[4-(hydroxymethyl)-1-piperidyl]methyl]phenyl]ethynyl]-7-methyl-indazol-2-yl]-2-(5,5-dimethyl-6,7-dihydropyrrolo[1,2-c]imidazol-1-yl)-N-thiazol-2-yl-acetamide

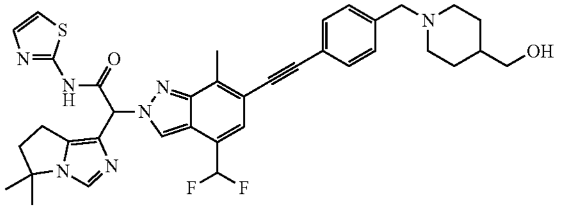 [SMILES: Cc1c(C#Cc2ccc(CN3CCC(CO)CC3)cc2)cc(C(F)F)c2cn(C(C(=O)Nc3nccs3)c3ncn4c3CCC4(C)C)nc12]

The title compound was obtained as a light yellow solid, MS: m/e=684.7 (M+H$^+$), using chemistry similar to that described in Example 1, step 8 starting from 2-[4-(difluoromethyl)-6-[2-(4-formylphenyl)ethynyl]-7-methyl-indazol-2-yl]-2-(5,5-dimethyl-6,7-dihydropyrrolo[1,2-c]imidazol-1-yl)-N-thiazol-2-yl-acetamide (Example 5, step 4) and piperidin-4-ylmethanol.

EXAMPLE 6

2-[4-(Difluoromethyl)-6-[2-[4-[[4-(hydroxymethyl)-1-piperidyl]methyl]phenyl]ethynyl]-7-methyl-indazol-2-yl]-2-(5-ethyl-5-methyl-6,7-dihydropyrrolo[1,2-c]imidazol-1-yl)-N-thiazol-2-yl-acetamide

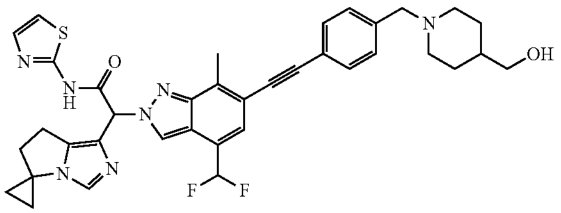 [SMILES: Cc1c(C#Cc2ccc(CN3CCC(CO)CC3)cc2)cc(C(F)F)c2cn(C(C(=O)Nc3nccs3)c3ncn4c3CCC43CC3)nc12]

Step 1: (5S)-5-[2-[6-Bromo-4-(difluoromethyl)-7-methyl-indazol-2-yl]-3-ethoxy-3-keto-propanoyl]-4-azaspiro[2.4]heptane-4-carboxylic acid tert-butyl ester

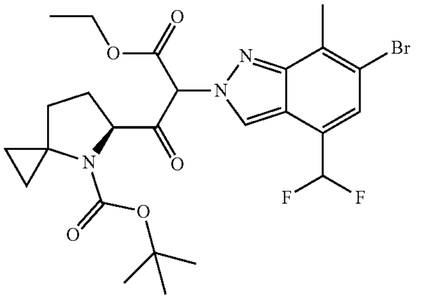 [SMILES: CCOC(=O)C(C(=O)[C@@H]1CCC2(CC2)N1C(=O)OC(C)(C)C)n1cc2c(C(F)F)cc(Br)c(C)c2n1]

In analogy to Example 1, step 4, (5S)-4-tert-butoxycarbonyl-4-azaspiro[2.4]heptane-5-carboxylic acid was treated with carbonyldiimidazole to give solution A. 2-[6-Bromo-4-(difluoromethyl)-7-methyl-indazol-2-yl]acetic acid ethyl ester was deprotonated with LDA and treated with solution A at −78° C. After stirring at room temperature overnight and workup in analogy to Example 1, step 4, the crude title compound was obtained as a light yellow foam and used for the next step without further purification. MS: m/e=572.3 ([M+H]$^+$)

Step 2: 2-[6-Bromo-4-(difluoromethyl)-7-methyl-indazol-2-yl]-2-spiro[6,7-dihydropyrrol[1,2-c]imidazole-5,1'-cyclopropane]-1-yl-acetic acid ethyl ester

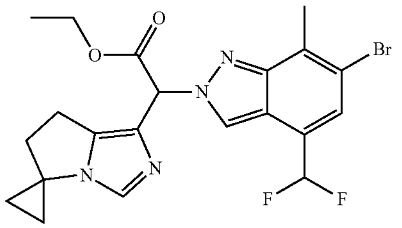 [SMILES: CCOC(=O)C(c1ncn2c1CCC21CC1)n1cc2c(C(F)F)cc(Br)c(C)c2n1]

In analogy to Example 1, step 5, (5S)-5-[2-[6-bromo-4-(difluoromethyl)-7-methyl-indazol-2-yl]-3-ethoxy-3-keto-propanoyl]-4-azaspiro[2.4]heptane-4-carboxylic acid tert-butyl ester was deprotected using HCl in dioxane followed by reaction with potassium thiocyanate to give the crude intermediate which was used for the next step without further purification.

In analogy to Example 1, step 6, the intermediate was treated with hydrogen peroxide in AcOH to give the title compound as a light yellow foam. MS: m/e=481.2 ([M+H]$^+$)

Step 3: 2-[6-Bromo-4-(difluoromethyl)-7-methyl-indazol-2-yl]-2-spiro[6,7-dihydropyrrol[1,2-c]imidazole-5,1'-cyclopropane]-1-yl-N-thiazol-2-yl-acetamide

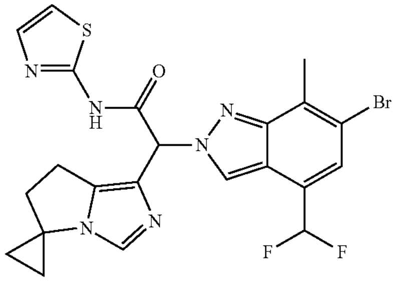 [SMILES: Cc1c(Br)cc(C(F)F)c2cn(C(C(=O)Nc3nccs3)c3ncn4c3CCC43CC3)nc12]

The title compound was obtained as a light yellow foam, MS: m/e=535.0 (M+H$^+$), using chemistry similar to that described in Example 1, step 7 starting from 2-[6-bromo-4-(difluoromethyl)-7-methyl-indazol-2-yl]-2-spiro[6,7-dihydropyrrol[1,2-c]imidazole-5,1'-cyclopropane]-1-yl-acetic acid ethyl ester (Example 6, step 2) and thiazol-2-amine.

Step 4: 2-[4-(Difluoromethyl)-6-[2-(4-formylphenyl)ethynyl]-7-methyl-indazol-2-yl]-2-spiro[6,7-dihydropyrrol[1,2-c]imidazole-5,1'-cyclopropane]-1-yl-N-thiazol-2-yl-acetamide

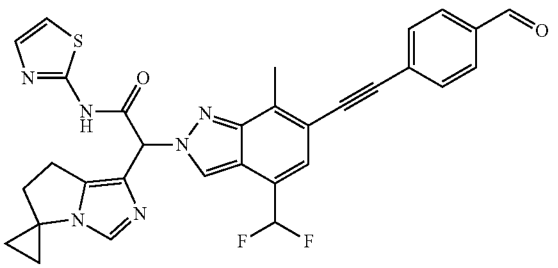 [SMILES: Cc1c(C#Cc2ccc(C=O)cc2)cc(C(F)F)c2cn(C(C(=O)Nc3nccs3)c3ncn4c3CCC43CC3)nc12]

The title compound was obtained as a dark brown amorphous, MS: m/e=583.3 (M+H$^+$), using chemistry similar to that described in Example 1, step 10 starting from 2-[6-bromo-4-(difluoromethyl)-7-methyl-indazol-2-yl]-2-spiro[6,7-dihydropyrrol[1,2-c]imidazole-5,1'-cyclopropane]-1-yl-N-thiazol-2-yl-acetamide (Example 6, step 3) and 4-ethynylbenzaldehyde.

Step 5: 2-[4-(Difluoromethyl)-6-[2-[4-[[4-(hydroxymethyl)-1-piperidyl]methyl]phenyl]ethynyl]-7-methyl-indazol-2-yl]-2-(5-ethyl-5-methyl-6,7-dihydropyrrolo[1,2-c]imidazol-1-yl)-N-thiazol-2-yl-acetamide

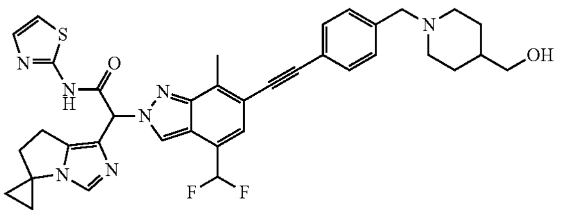 [SMILES: Cc1c(C#Cc2ccc(CN3CCC(CO)CC3)cc2)cc(C(F)F)c2cn(C(C(=O)Nc3nccs3)c3ncn4c3CCC43CC3)nc12]

The title compound was obtained as a light yellow solid, MS: m/e=682.5 (M+H$^+$), using chemistry similar to that described in Example 1, step 8 starting from 2-[4-(difluoromethyl)-6-[2-(4-formylphenyl)ethynyl]-7-methyl-indazol-2-yl]-2-spiro[6,7-dihydropyrrol[1,2-c]imidazole-5,1'-cyclopropane]-1-yl-N-thiazol-2-yl-acetamide (Example 6, step 4) and piperidin-4-ylmethanol.

EXAMPLE 7

2-(5-Ethyl-5-methyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide

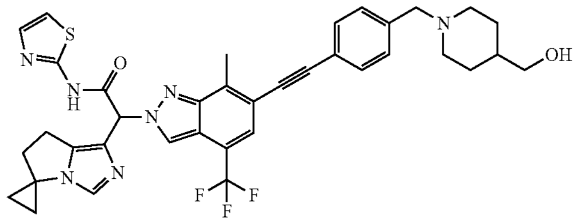 [SMILES: Cc1c(C#Cc2ccc(CN3CCC(CO)CC3)cc2)cc(C(F)(F)F)c2cn(C(C(=O)Nc3nccs3)c3ncn4c3CCC43CC3)nc12]

Step 1: tert-Butyl (5S)-5-[2-[6-bromo-7-methyl-4-(trifluoromethyl)indazol-2-yl]-3-ethoxy-3-oxo-propanoyl]-4-azaspiro[2.4]heptane-4-carboxylate

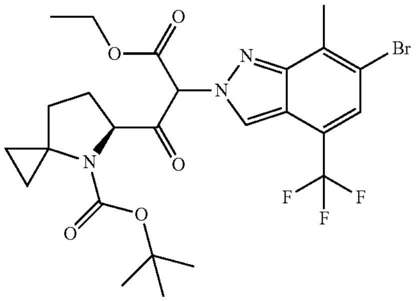 [SMILES: CCOC(=O)C(C(=O)[C@@H]1CCC2(CC2)N1C(=O)OC(C)(C)C)n1cc2c(C(F)(F)F)cc(Br)c(C)c2n1]

In analogy to Example 1, step 4, (5S)-4-tert-butoxycarbonyl-4-azaspiro[2.4]heptane-5-carboxylic acid was treated with carbonyldiimidazole to give solution A. Ethyl 2-(6-bromo-7-methyl-4-(trifluoromethyl)-2H-indazol-2-yl)acetate was deprotonated with LDA and treated with solution A at −78° C. After stirring at room temperature overnight and workup in analogy to Example 1, step 4, the crude title compound was obtained as a light brown foam and used for the next step without further purification. MS: m/e=590.3 ($[M+H]^+$)

Step 2: Ethyl 2-[6-bromo-7-methyl-4-(trifluoromethyl)indazol-2-yl]-2-(5-ethyl-5-methyl-6,7-dihydropyrrolo[1,2-c]imidazol-1-yl)acetate

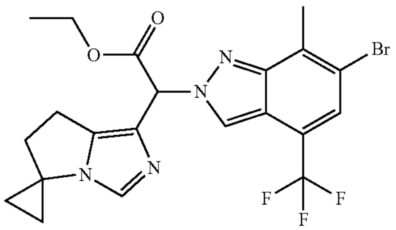 [SMILES: CCOC(=O)C(c1ncn2c1CCC21CC1)n1cc2c(C(F)(F)F)cc(Br)c(C)c2n1]

In analogy to Example 1, step 5, tert-Butyl (5S)-5-[2-[6-bromo-7-methyl-4-(trifluoromethyl)indazol-2-yl]-3-ethoxy-3-oxo-propanoyl]-4-azaspiro[2.4]heptane-4-carboxylate was deprotected using HCl in dioxane followed by reaction with potassium thiocyanate to give the crude intermediate which was used for the next step without further purification.

In analogy to Example 1, step 6, the intermediate was treated with hydrogen peroxide in AcOH to give the title compound as a white foam. MS: m/e=499.2 ($[M+H]^+$)

Step 3: 2-[6-Bromo-7-methyl-4-(trifluoromethyl)indazol-2-yl]-2-(5-ethyl-5-methyl-6,7-dihydropyrrolo[1,2-c]imidazol-1-yl)-N-thiazol-2-yl-acetamide

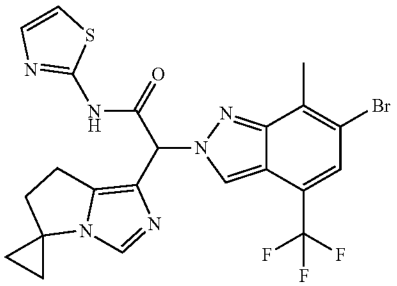 [SMILES: Cc1c(Br)cc(C(F)(F)F)c2cn(C(C(=O)Nc3nccs3)c3ncn4c3CCC43CC3)nc12]

The title compound was obtained as a light yellow foam, MS: m/e=552.9 ($M+H^+$), using chemistry similar to that described in Example 1, step 7 starting from ethyl 2-[6-bromo-7-methyl-4-(trifluoromethyl)indazol-2-yl]-2-(5-ethyl-5-methyl-6,7-dihydropyrrolo[1,2-c]imidazol-1-yl)acetate (Example 7, step 2) and thiazol-2-amine.

Step 4: 2-[6-[2-(4-Formylphenyl)ethynyl]-7-methyl-4-(trifluoromethyl)indazol-2-yl]-2-spiro[6,7-dihydropyrrolo[1,2-c]imidazole-5,1'-cyclopropane]-1-yl-N-thiazol-2-yl-acetamide

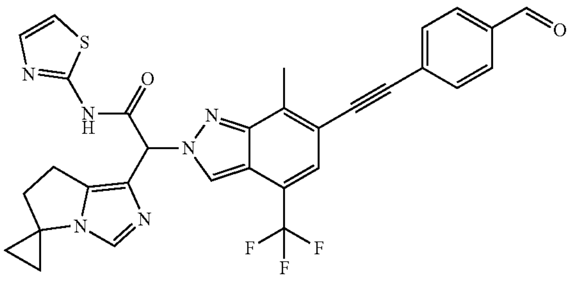 [SMILES: Cc1c(C#Cc2ccc(C=O)cc2)cc(C(F)(F)F)c2cn(C(C(=O)Nc3nccs3)c3ncn4c3CCC43CC3)nc12]

The title compound was obtained as a dark brown foam, MS: m/e=601.4 ($M+H^+$), using chemistry similar to that described in Example 1, step 10 starting from 2-[6-bromo-7-methyl-4-(trifluoromethyl)indazol-2-yl]-2-(5-ethyl-5-methyl-6,7-dihydropyrrolo[1,2-c]imidazol-1-yl)-N-thiazol-2-yl-acetamide (Example 7, step 3) and 4-ethynylbenzaldehyde.

Step 5: 2-(5-Ethyl-5-methyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide

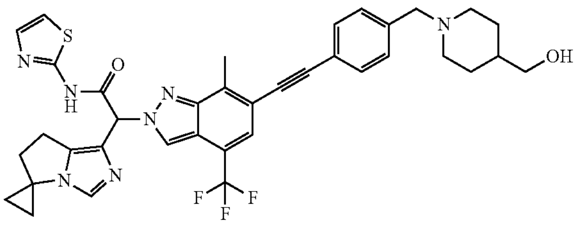 [SMILES: Cc1c(C#Cc2ccc(CN3CCC(CO)CC3)cc2)cc(C(F)(F)F)c2cn(C(C(=O)Nc3nccs3)c3ncn4c3CCC43CC3)nc12]

The title compound was obtained as a light yellow solid, MS: m/e=700.6 (M+H$^+$), using chemistry similar to that described in Example 1, step 8 starting from 2-[6-[2-(4-formylphenyl)ethynyl]-7-methyl-4-(trifluoromethyl)indazol-2-yl]-2-spiro[6,7-dihydropyrrolo[1,2-c]imidazole-5,1'-cyclopropane]-1-yl-N-thiazol-2-yl-acetamide (Example 7, step 4) and piperidin-4-ylmethanol.

EXAMPLE 8

2-(5,5-Dimethyl-6,7-dihydropyrrolo[1,2-c]imidazol-1-yl)-2-[6-[2-[4-[[4-(hydroxymethyl)-1-piperidyl]methyl]phenyl]ethynyl]-7-methyl-4-(trifluoromethyl)indazol-2-yl]-N-thiazol-2-yl-acetamide

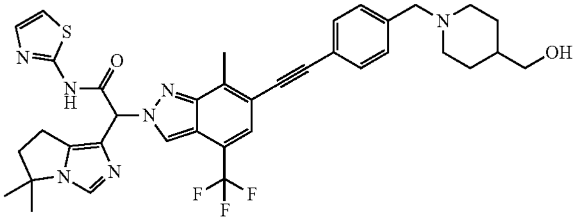 [SMILES: Cc1c(C#Cc2ccc(CN3CCC(CO)CC3)cc2)cc(C(F)(F)F)c2cn(C(C(=O)Nc3nccs3)c3ncn4c3CCC4(C)C)nc12]

Step 1: 5-[2-[6-Bromo-7-methyl-4-(trifluoromethyl)indazol-2-yl]-3-ethoxy-3-keto-propanoyl]-2,2-dimethyl-pyrrolidine-1-carboxylic acid tert-butyl ester

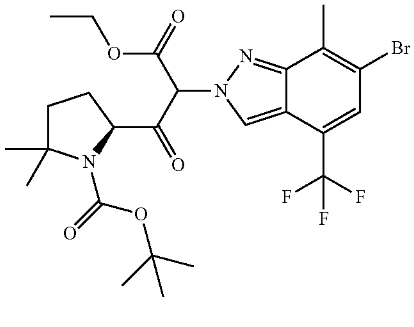 [SMILES: CCOC(=O)C(C(=O)[C@@H]1CCC(C)(C)N1C(=O)OC(C)(C)C)n1cc2c(C(F)(F)F)cc(Br)c(C)c2n1]

In analogy to Example 1, step 4, (2S)-1-tert-butoxycarbonyl-5,5-dimethyl-proline was treated with carbonyldiimidazole to give solution A. Ethyl 2-(6-bromo-7-methyl-4-(trifluoromethyl)-2H-indazol-2-yl)acetate was deprotonated with LDA and treated with solution A at −78° C. After stirring at room temperature overnight and workup in analogy to Example 1, step 4, the crude title compound was obtained as a light brown foam and used for the next step without further purification. MS: m/e=590.3 ([M+H]$^+$)

Step 2: 2-[6-Bromo-7-methyl-4-(trifluoromethyl)indazol-2-yl]-2-(5,5-dimethyl-6,7-dihydropyrrol[1,2-c]imidazol-1-yl)acetic acid ethyl ester

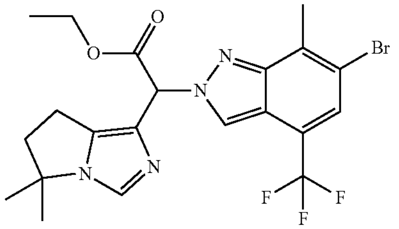 [SMILES: CCOC(=O)C(c1ncn2c1CCC2(C)C)n1cc2c(C(F)(F)F)cc(Br)c(C)c2n1]

In analogy to Example 1, step 5, 5-[2-[6-bromo-7-methyl-4-(trifluoromethyl)indazol-2-yl]-3-ethoxy-3-keto-propanoyl]-2,2-dimethyl-pyrrolidine-1-carboxylic acid tert-butyl ester was deprotected using HCl in dioxane followed by reaction with potassium thiocyanate to give the crude intermediate which was used for the next step without further purification.

In analogy to Example 1, step 6, the intermediate was treated with hydrogen peroxide in AcOH to give the title compound as a light yellow foam. MS: m/e=501.2 ([M+H]$^+$)

Step 3: 2-[6-Bromo-7-methyl-4-(trifluoromethyl)indazol-2-yl]-2-(5,5-dimethyl-6,7-dihydropyrrol[1,2-c]imidazol-1-yl)-N-thiazol-2-yl-acetamide

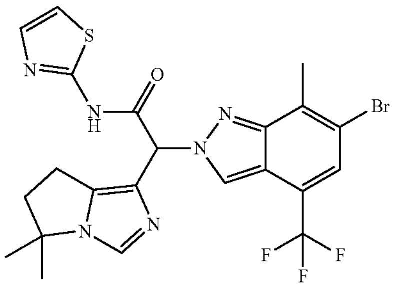 [SMILES: Cc1c(Br)cc(C(F)(F)F)c2cn(C(C(=O)Nc3nccs3)c3ncn4c3CCC4(C)C)nc12]

The title compound was obtained as a light yellow foam, MS: m/e=555.1 (M+H$^+$), using chemistry similar to that described in Example 1, step 7 starting from 2-[6-bromo-7-methyl-4-(trifluoromethyl)indazol-2-yl]-2-(5,5-dimethyl-6,7-dihydropyrrol[1,2-c]imidazol-1-yl)acetic acid ethyl ester (Example 8, step 2) and thiazol-2-amine.

Step 4: 2-(5,5-Dimethyl-6,7-dihydropyrrol[1,2-c]imidazol-1-yl)-2-[6-[2-(4-formylphenyl)ethynyl]-7-methyl-4-(trifluoromethyl)indazol-2-yl]-N-thiazol-2-yl-acetamide

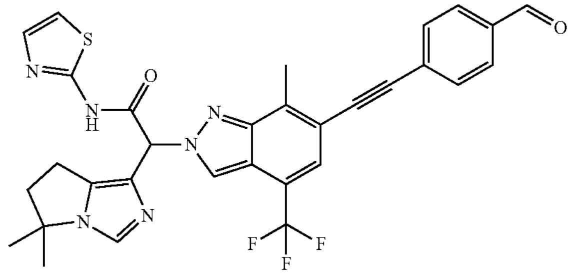 [SMILES: Cc1c(C#Cc2ccc(C=O)cc2)cc(C(F)(F)F)c2cn(C(C(=O)Nc3nccs3)c3ncn4c3CCC4(C)C)nc12]

The title compound was obtained as a dark brown foam, MS: m/e=603.4 (M+H$^+$), using chemistry similar to that described in Example 1, step 10 starting from 2-[6-bromo-7-methyl-4-(trifluoromethyl)indazol-2-yl]-2-(5,5-dimethyl-6,7-dihydropyrrol[1,2-c]imidazol-1-yl)-N-thiazol-2-yl-acetamide (Example 8, step 3) and 4-ethynylbenzaldehyde.

Step 5: 2-[4-(Difluoromethyl)-6-[2-[4-[[4-(hydroxymethyl)-1-piperidyl]methyl]phenyl]ethynyl]-7-methyl-indazol-2-yl]-2-(5,5-dimethyl-6,7-dihydropyrrolo[1,2-c]imidazol-1-yl)-N-thiazol-2-yl-acetamide

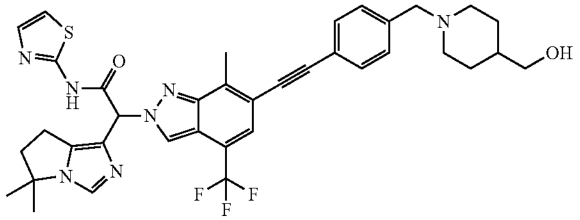 [SMILES: Cc1c(C#Cc2ccc(CN3CCC(CO)CC3)cc2)cc(C(F)(F)F)c2cn(C(C(=O)Nc3nccs3)c3ncn4c3CCC4(C)C)nc12]

The title compound was obtained as a light yellow solid, MS: m/e=702.5 (M+H$^+$), using chemistry similar to that described in Example 1, step 8 starting from 2-(5,5-dimethyl-6,7-dihydropyrrol[1,2-c]imidazol-1-yl)-2-[6-[2-(4-formylphenyl)ethynyl]-7-methyl-4-(trifluoromethyl)indazol-2-yl]-N-thiazol-2-yl-acetamide (Example 8, step 4) and piperidin-4-ylmethanol.

EXAMPLE 9

HTRF Phospho EGFR LRCS Assay (Cellular)

Cell Line and Media

BaF3-LRCS cell line were obtained from Crownbio (San Diego, CA, USA). Cells were maintained at 37° C., 5% C02 in RPMI ATCC (Gibco 31870)+2 mM Glutamine+0.5 µg/ml Puromycin supplemented with 10% fetal bovine serum (FBS) (Gibco).

Protocol

Cells are transferred as above to Greiner Bio-One, Nr. 784-08 micro-titerplate at 20000 cells/well in 12.5 µl of growth medium/well after the plates had been pre-filled with 12.5 nl of DMSO solutions of the to be tested compounds (in dose response) or DMSO only. After spinning the plates at 300×g for 30 seconds the cells were incubated for 4 hours at 37 C, 5% C02, 95% humidity. The cells were lysed by adding to the compound mix 4 l/well of the supplemented lysis buffer (Cis-bio, Phospho-EGFR HTRF kit, 64EG1PEH), followed by incubation for 30 min at room temperature with shaking (400 rpm). The plates were then frozen and stored overnight at −80° C. On the next day and after thawing the plates, 4 µl of a mixture of anti-Phospho-EGFR Cryptate and of anti-Phospho-EGFR-d2 antibody solutions prepared in the supplied detection buffer was added to each well. The lidded plates were then incubated for 4 h at room temperature before reading the fluorescence emission at 616 and 665 nm using an Envision reader (Perkin Elmer). Data was analyzed in similar fashion as above using the normalized ratio of the 665 to 616 signals multiplied by 10000.

The results are shown in Table 1.

TABLE 8

BaF3 cellular HTRF Phospho EGFR LRCS assay data

| Exam. | Structure | $IC_{50}$ (BaF3 LRCS) |
|---|---|---|
| 1 | 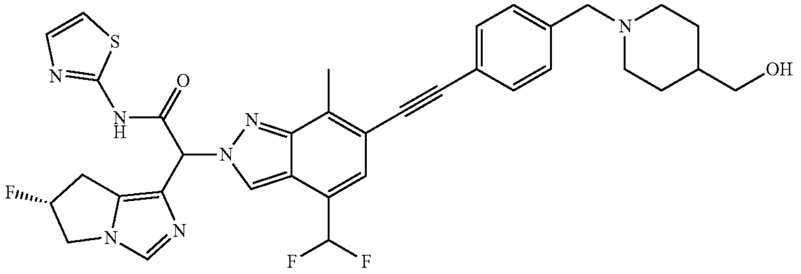 [SMILES: Cc1c(C#Cc2ccc(CN3CCC(CO)CC3)cc2)cc(C(F)F)c2cn(C(C(=O)Nc3nccs3)c3ncn4c3C[C@@H](F)C4)nc12] | 22 nM |

TABLE 8-continued
BaF3 cellular HTRF Phospho EGFR LRCS assay data
| Exam. | Structure | $IC_{50}$ (BaF3 LRCS) |
| --- | --- | --- |
| 2 | 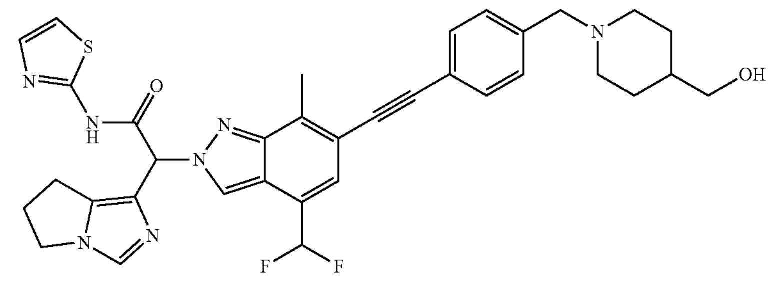 [SMILES: Cc1c(C#Cc2ccc(CN3CCC(CO)CC3)cc2)cc(C(F)F)c2cn(C(C(=O)Nc3nccs3)c3ncn4c3CCC4)nc12] | 23 nM |
| 3 | 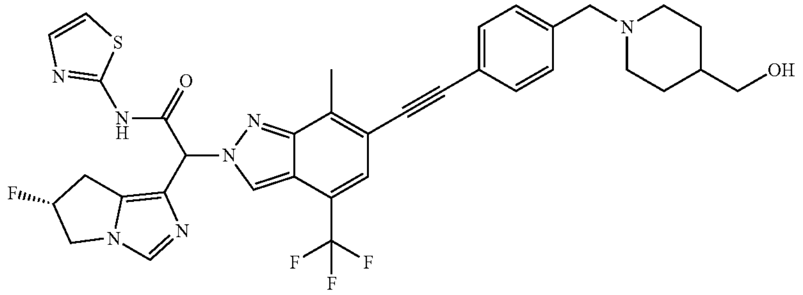 [SMILES: Cc1c(C#Cc2ccc(CN3CCC(CO)CC3)cc2)cc(C(F)(F)F)c2cn(C(C(=O)Nc3nccs3)c3ncn4c3C[C@@H](F)C4)nc12] | 15 nM |
| 4 | 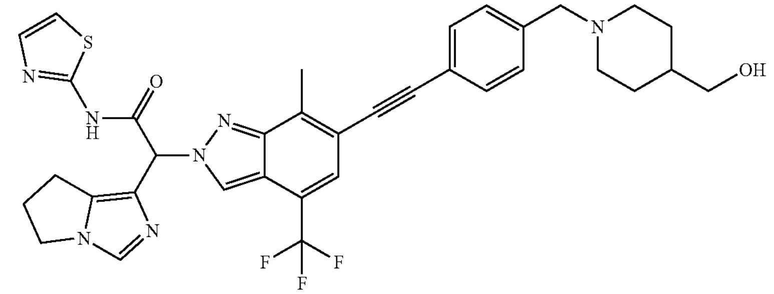 [SMILES: Cc1c(C#Cc2ccc(CN3CCC(CO)CC3)cc2)cc(C(F)(F)F)c2cn(C(C(=O)Nc3nccs3)c3ncn4c3CCC4)nc12] | 9 nM |
| 5 | 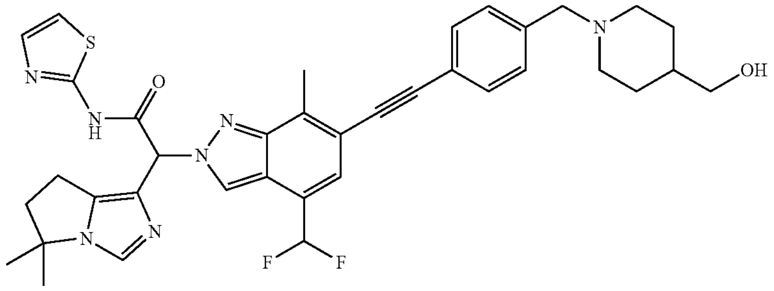 [SMILES: Cc1c(C#Cc2ccc(CN3CCC(CO)CC3)cc2)cc(C(F)F)c2cn(C(C(=O)Nc3nccs3)c3ncn4c3CCC4(C)C)nc12] | 11 nM |
| 6 | 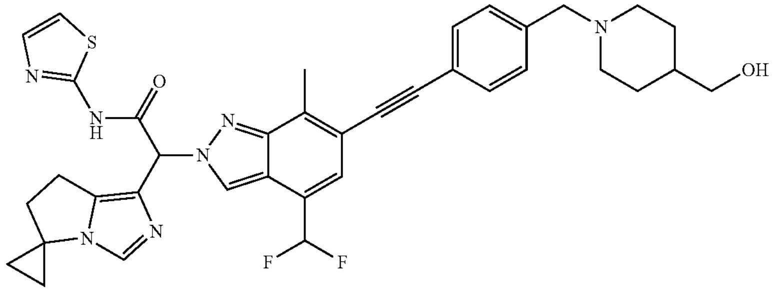 [SMILES: Cc1c(C#Cc2ccc(CN3CCC(CO)CC3)cc2)cc(C(F)F)c2cn(C(C(=O)Nc3nccs3)c3ncn4c3CCC43CC3)nc12] | 10 nM |

TABLE 8-continued

| BaF3 cellular HTRF Phospho EGFR LRCS assay data | | |
|---|---|---|
| Exam. | Structure | $IC_{50}$ (BaF3 LRCS) |
| 7 | 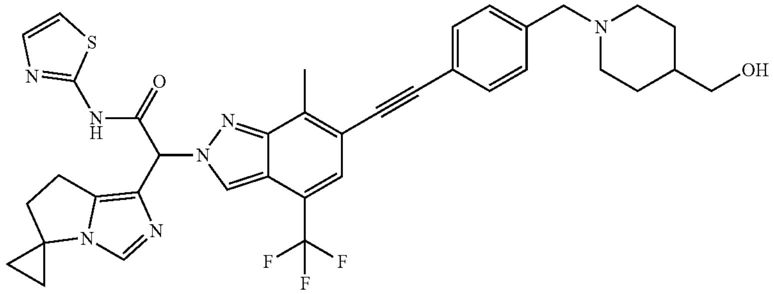 [SMILES: Cc1c(C#Cc2ccc(CN3CCC(CO)CC3)cc2)cc(C(F)(F)F)c2cn(C(C(=O)Nc3nccs3)c3ncn4c3CCC43CC3)nc12] | 11 nM |
| 8 | 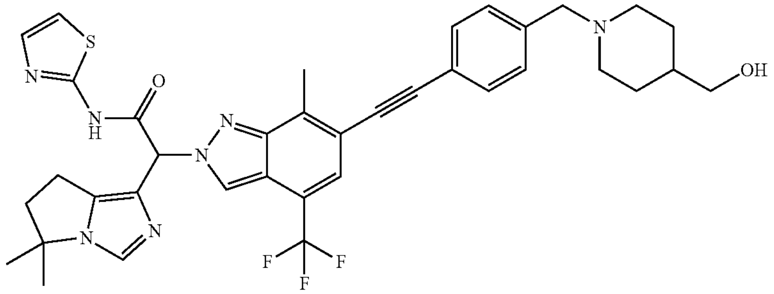 [SMILES: Cc1c(C#Cc2ccc(CN3CCC(CO)CC3)cc2)cc(C(F)(F)F)c2cn(C(C(=O)Nc3nccs3)c3ncn4c3CCC4(C)C)nc12] | 12 nM |

The invention claimed is:

1. A compound of formula (I)

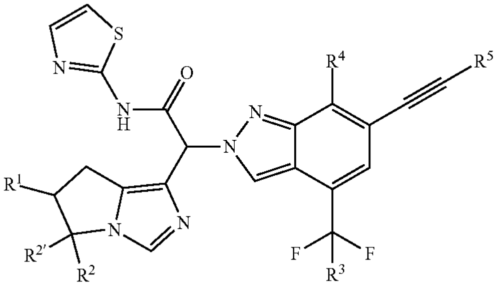

(I)

wherein $R^1$ is hydrogen or halogen;

$R^2$ and $R^{2'}$ are independently selected from hydrogen and alkyl;

or $R^2$ and $R^{2'}$, together with the carbon atom to which they are attached, form cycloalkyl;

$R^3$ is hydrogen or halogen;

$R^4$ is alkyl; and $R^5$ is hydroxyalkyl(heterocycloalkyl)alkyl;

or a pharmaceutically acceptable salt thereof.

2. The compound according to claim 1, or a pharmaceutically acceptable salt thereof, wherein $R^1$ is hydrogen or fluoro.

3. The compound according to claim 1, or a pharmaceutically acceptable salt thereof, wherein $R^1$ is hydrogen.

4. The compound according to claim 1, or a pharmaceutically acceptable salt thereof, wherein $R^2$ and $R^{2'}$ are independently selected from hydrogen or methyl; or $R^2$ and $R^{2'}$, together with the carbon atom to which they are attached, form cyclopropyl.

5. The compound according to claim 1, or a pharmaceutically acceptable salt thereof, wherein $R^2$ and $R^{2'}$ are both alkyl at the same time; or $R^2$ and $R^{2'}$, together with the carbon atom to which they are attached, form cycloalkyl.

6. The compound according to claim 1, or a pharmaceutically acceptable salt thereof, wherein $R^2$ and $R^{2'}$ are both methyl; or $R^2$ and $R^{2'}$, together with the carbon atom to which they are attached, form cyclopropyl.

7. The compound according to claim 1, or a pharmaceutically acceptable salt thereof, wherein $R^3$ is hydrogen or fluoro.

8. The compound according to claim 1, or a pharmaceutically acceptable salt thereof, wherein $R^4$ is methyl.

9. The compound according to claim 1, or a pharmaceutically acceptable salt thereof, wherein $R^5$ is hydroxyalkyl (piperidinyl)alkyl.

10. The compound according to claim 1, or a pharmaceutically acceptable salt thereof, wherein $R^5$ is hydroxymethyl(piperidinyl)methyl.

11. The compound according to claim 1, or a pharmaceutically acceptable salt thereof, wherein the compound is selected from the group consisting of:

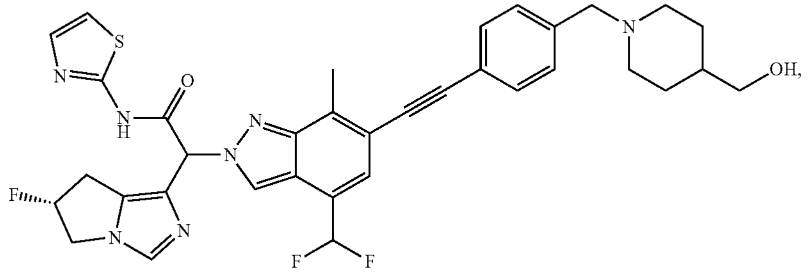
,
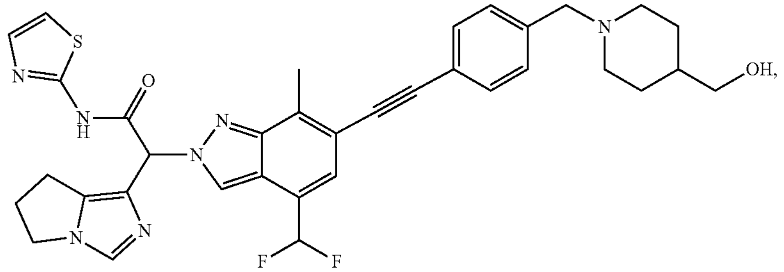
,
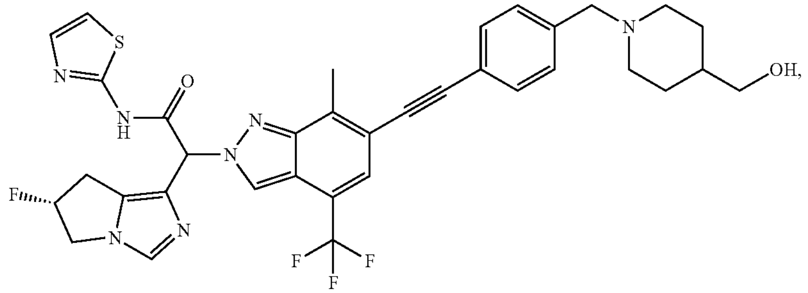
,
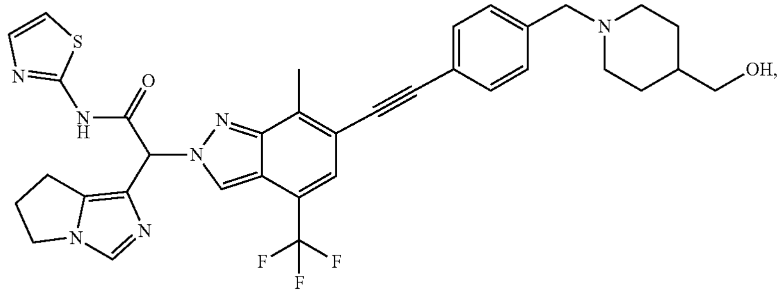
,
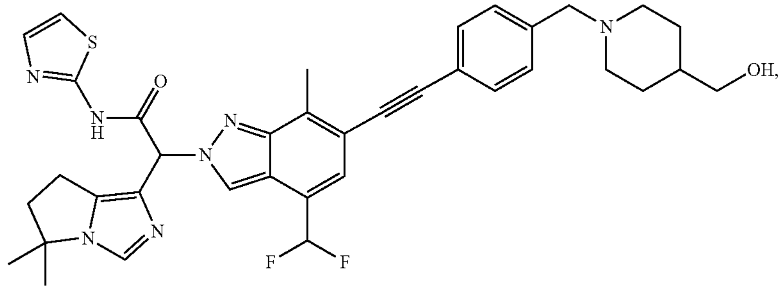 [SMILES: Cc1c(C#Cc2ccc(CN3CCC(CO)CC3)cc2)cc(C(F)F)c2cn(C(C(=O)Nc3nccs3)c3ncn4c3CCC4(C)C)nc12]
,
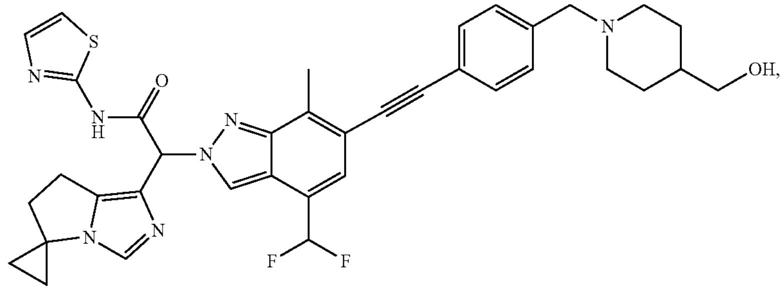 [SMILES: Cc1c(C#Cc2ccc(CN3CCC(CO)CC3)cc2)cc(C(F)F)c2cn(C(C(=O)Nc3nccs3)c3ncn4c3CCC4(C)C)nc12]
,

-continued
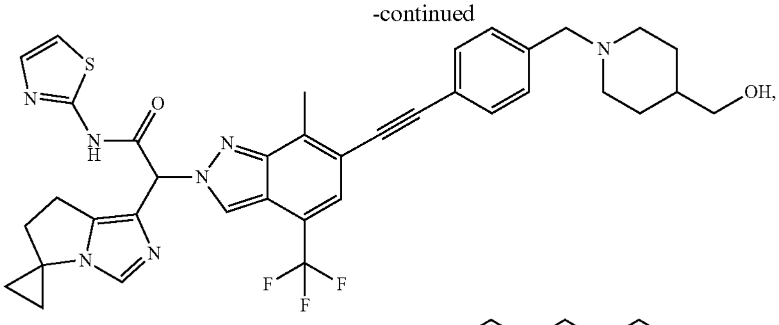
, and
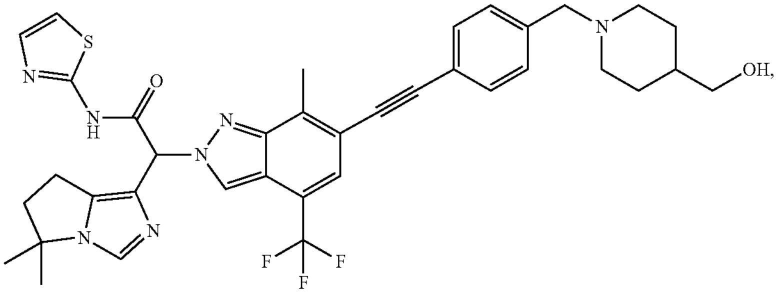 [SMILES: Cc1c(C#Cc2ccc(CN3CCC(CO)CC3)cc2)cc(C(F)(F)F)c2cn(C(C(=O)Nc3nccs3)c3ncn4c3CCC43CC3)nc12]
,
or a pharmaceutically acceptable salt thereof.
12. The compound according to claim 1, or a pharmaceutically acceptable salt thereof, wherein the compound is selected from the group consisting of:
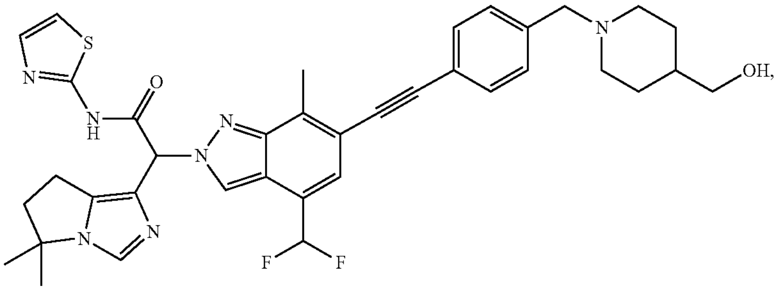
,
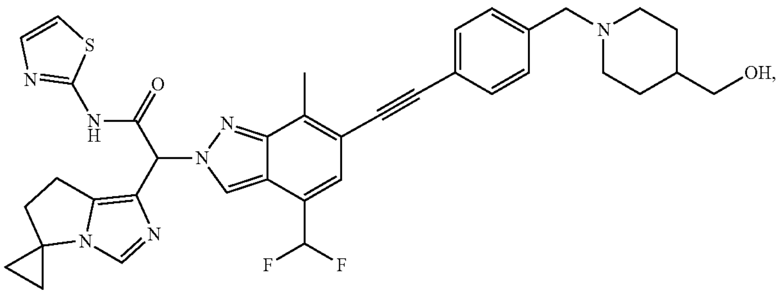
,
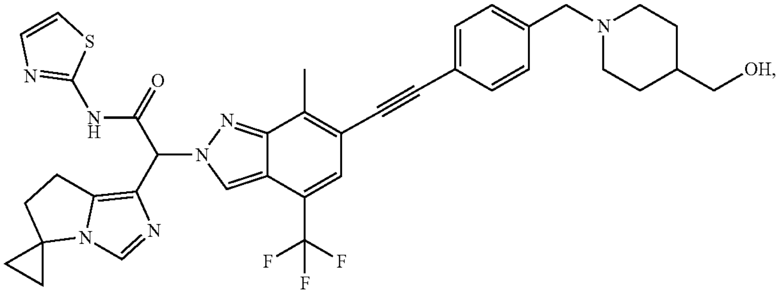 [SMILES: Cc1c(C#Cc2ccc(CN3CCC(CO)CC3)cc2)cc(C(F)(F)F)c2cn(C(C(=O)Nc3nccs3)c3ncn4c3CCC43CC3)nc12]
, and -continued

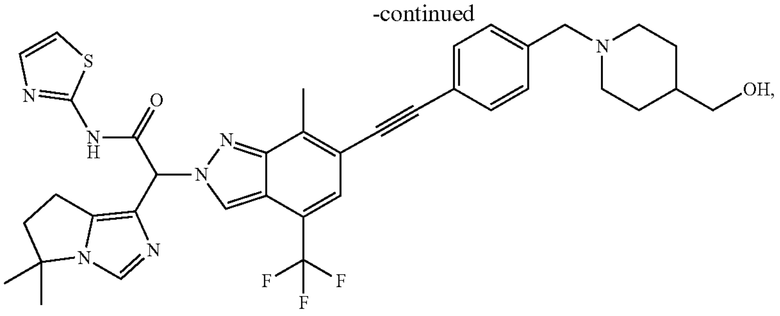

or a pharmaceutically acceptable salt thereof.

13. The compound of claim 1, or a pharmaceutically acceptable salt thereof, wherein the compound of formula (I) is

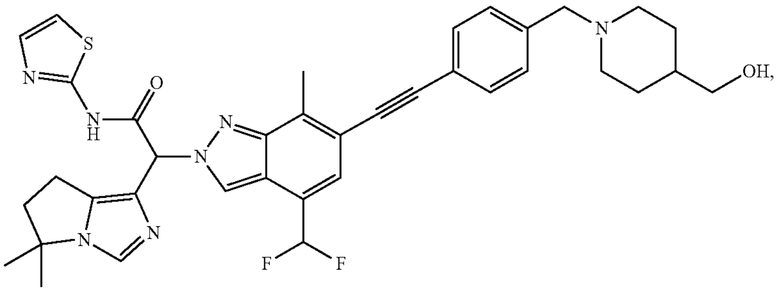 [SMILES: Cc1c(C#Cc2ccc(CN3CCC(CO)CC3)cc2)cc(C(F)F)c2cn(C(C(=O)Nc3nccs3)c3ncn4c3CCC4(C)C)nc12]

or a pharmaceutically acceptable salt thereof.

14. The compound of claim 1, or a pharmaceutically acceptable salt thereof, wherein the compound of formula (I) is

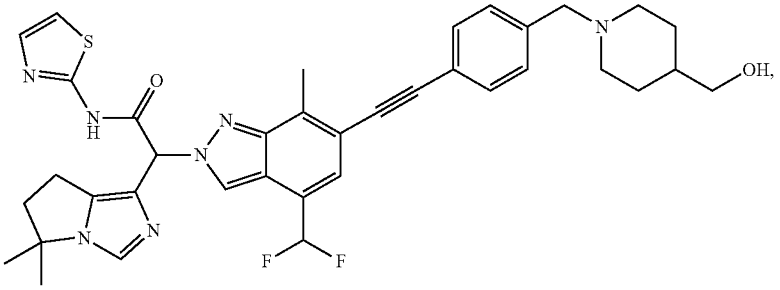 [SMILES: Cc1c(C#Cc2ccc(CN3CCC(CO)CC3)cc2)cc(C(F)F)c2cn(C(C(=O)Nc3nccs3)c3ncn4c3CCC4(C)C)nc12]

or a pharmaceutically acceptable salt thereof.

15. The compound of claim 1, or a pharmaceutically acceptable salt thereof, wherein the compound of formula (I) is

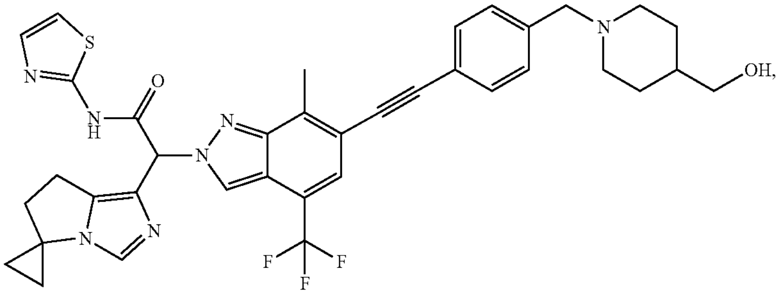 [SMILES: Cc1c(C#Cc2ccc(CN3CCC(CO)CC3)cc2)cc(C(F)(F)F)c2cn(C(C(=O)Nc3nccs3)c3ncn4c3CCC43CC3)nc12]

or a pharmaceutically acceptable salt thereof.

16. The compound of claim 1, or a pharmaceutically acceptable salt thereof, wherein the compound of formula (I) is

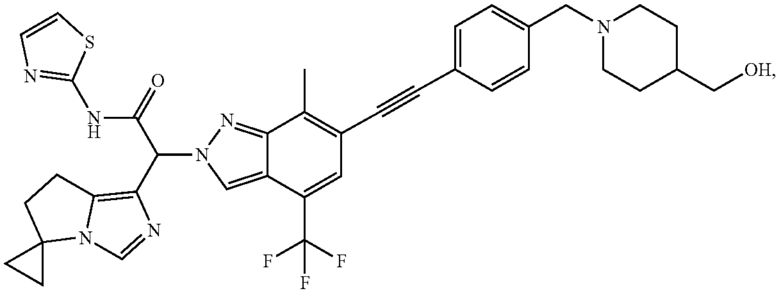 [SMILES: Cc1c(C#Cc2ccc(CN3CCC(CO)CC3)cc2)cc(C(F)(F)F)c2cn(C(C(=O)Nc3nccs3)c3ncn4c3CCC43CC3)nc12]

or a pharmaceutically acceptable salt thereof.

17. The compound of claim 1, wherein the compound of formula (I) is

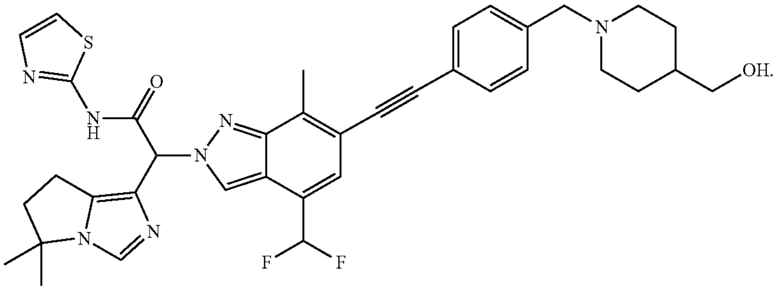

18. The compound of claim 1, wherein the compound of formula (I) is
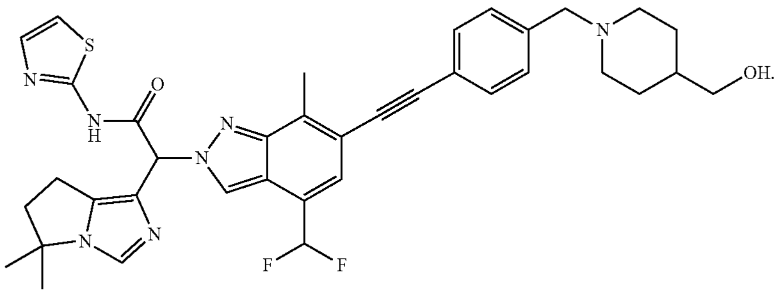
19. The compound of claim 1, wherein the compound of formula (I) is
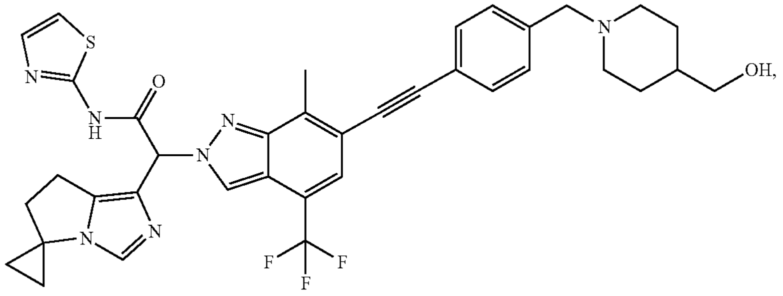
20. The compound of claim 1, wherein the compound of formula (I) is
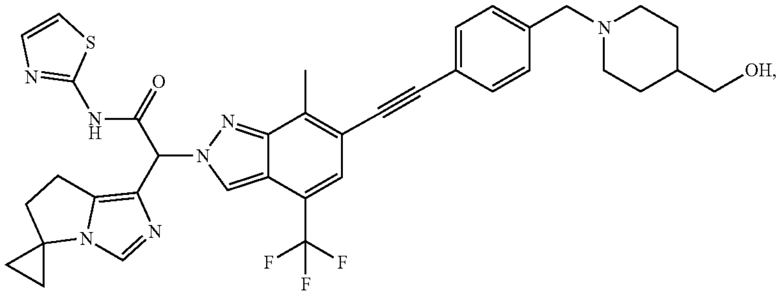

21. A pharmaceutical composition comprising the compound or pharmaceutically acceptable salt according to claim 1 and a therapeutically inert carrier.

22. A process for the preparation of a compound of formula (I)

(I)

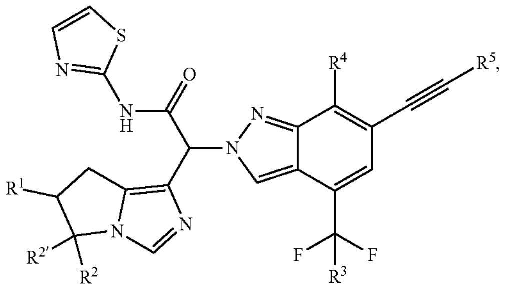

or a pharmaceutically acceptable salt thereof, comprising contacting a compound of formula (B1)

(B1)

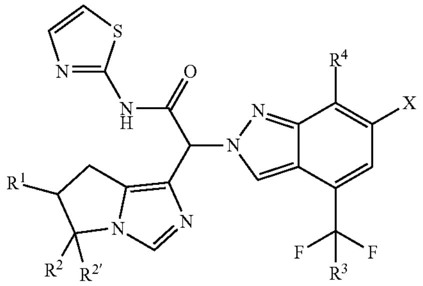

with a compound of formula (B2)

(B2)

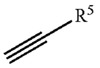

in the presence of a base, a Pd(II) catalyst and a Cu(I) salt, wherein $R^1$ is hydrogen or halogen;

$R^2$ and $R^{2'}$ are independently selected from hydrogen and alkyl;

or $R^2$ and $R^{2'}$, together with the carbon atom to which they are attached, form cycloalkyl;

$R^3$ is hydrogen or halogen;

$R^4$ is alkyl; and $R^5$ is hydroxyalkyl(heterocycloalkyl)alkyl; and

X is halogen.

23. A method for treating a non-small cell lung cancer (NSCLC) comprising one or more Epidermal Growth Factor Receptor (EGFR) mutations selected from T790M, L858R and C797S in a patient in need thereof, comprising administering an effective amount of the compound or pharmaceutically acceptable salt according to claim 1.

* * * * *